United States Patent [19]
Kanomi et al.

[11] Patent Number: 5,921,774
[45] Date of Patent: Jul. 13, 1999

[54] SUPPORTING BODY FOR USE IN ORTHODONTIC APPLIANCE AND METHOD

[75] Inventors: Ryuzo Kanomi, Himeji; Katsuyuki Nakagawa, Otawara, both of Japan

[73] Assignee: Sankin Kogyo kabushiki Kaisha, Otawara, Japan

[21] Appl. No.: 08/907,092

[22] Filed: Aug. 6, 1997

[30] Foreign Application Priority Data

Aug. 8, 1996 [JP] Japan .................................. 8-210108

[51] Int. Cl.$^6$ .............................. A61C 3/00; A61C 8/00
[52] U.S. Cl. ............................................. 433/18; 433/173
[58] Field of Search .................................. 433/173, 174, 433/175, 176, 172, 17, 18

[56] References Cited

U.S. PATENT DOCUMENTS

| | | | |
|---|---|---|---|
| 4,988,292 | 1/1991 | Rosen | 433/8 |
| 5,071,345 | 12/1991 | Rosen | 433/173 |
| 5,082,442 | 1/1992 | Rosen | 433/173 |
| 5,125,831 | 6/1992 | Pospisil | 433/18 |
| 5,232,364 | 8/1993 | Rosen | 433/173 |
| 5,292,248 | 3/1994 | Schultz | 433/17 |
| 5,697,779 | 12/1997 | Sachdeva et al. | 433/173 |

OTHER PUBLICATIONS

Journal of Orofacial Orthopedics, vol. 57, No. 3, pp. 142–153, H. Wehrbein, et al., "Das Orthosystem—Ein Neues Implantatsystem Zur Orthodontischen Verankerung Am Gaumen", 1996.

Case Report, vol. 30, No. 5, pp. 261–265, Frederic Bousquet, et al., "Use Of An Impacted Post For Anchorage", May 1996.

*Primary Examiner*—John J. Wilson
*Attorney, Agent, or Firm*—Oblon, Spivak, McClelland, Maier & Neustadt, P.C.

[57] ABSTRACT

The present invention provides a supporting body for use in an orthodontic appliance capable of applying a force to the tooth to be treated from the most preferable position. The supporting body includes an implant member having a maximum dimension across the thereof cross section of 2 mm or less for being implanted in a jaw bone (i.e. the maxilla and/or mandibula), and an exposed member forming one end of the supporting body to be exposed to inside of mouth. The exposed portion includes an extended arm and the arm is formed with a hook.

27 Claims, 25 Drawing Sheets

FIG. 13
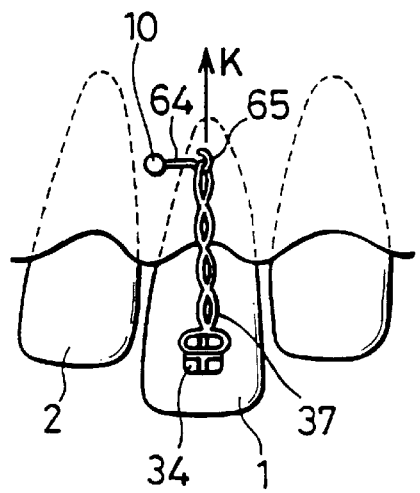
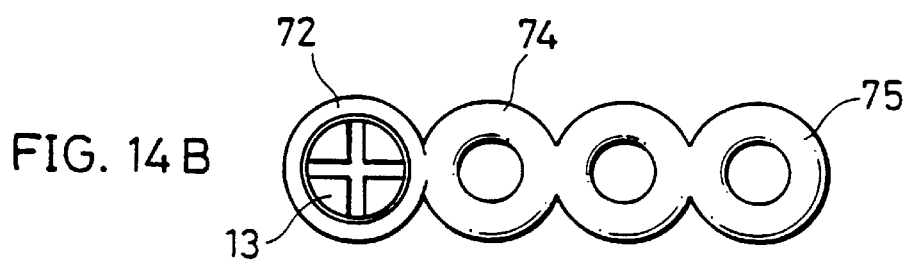
FIG. 14B
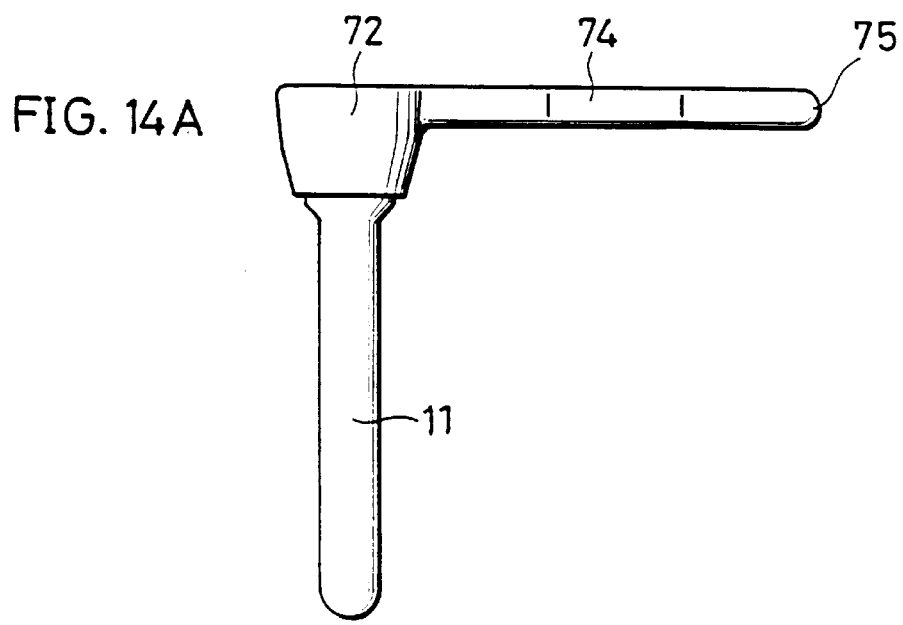
FIG. 14A

SUPPORTING BODY FOR USE IN ORTHODONTIC APPLIANCE AND METHOD

BACKGROUND OF THE INVENTION

1. Field of the Invention

The present invention relates to a supporting body for use n an orthodontic appliance which is used as an anchorage for giving a force to a tooth to be treated thereby moving it to a desired position, and an orthodontic method using the same.

2. Discussion of the Background

In recent years, in a field of dental treatment, various orthodontic treatments have been conducted to patients having dental malocclusion.

In the most well-known orthodontic treatment, brackets are fixedly attached on the surface of teeth by a bonding agent, and an arch wire is passed through the brackets. The restoring force generated by the arch wire pulls, pushes, or twists the teeth, so that the teeth are moved to the desired positions in the desired directions in a relative movement. In this manner, the alignment of all of the teeth is corrected. In addition to an arch wire, also used in an orthodontic treatment are rubber rings, resin chains, metallic coil springs, auxiliary wires and the like. As well as the arch wire, these members are engaged to brackets or lingual buttons fixedly attached to the teeth, so as to apply a force to the teeth.

In an orthodontic treatment in which a space between two teeth is closed by accomplishing a relative movement therebetween, a force is applied to these two teeth in a direction toward each other, so that they are moved toward each other. In this case, if the size of these two teeth are different from each other, movement of the larger tooth is smaller, and movement of the smaller tooth is larger.

In many cases, the larger tooth is used as an anchorage in treatment, because the movement of the larger tooth is thought to be smaller. Generally, a molar tooth, especially a first molar tooth (a sixth tooth) is used as an anchorage.

When an orthodontic treatment is conducted on a patient who has lost molar teeth, an artificial dental root (an implant member) is implanted to a portion having no molar teeth. The artificial dental tooth has an abutment on its top end with a path through which an arch wire is passed as shown in U.S. Pat. No. 4,988,292.

There is another technique in which a small implant member is implanted in a maxilla and/or mandibula (or simply referred to as a jaw bone) through an alveolus, and a supporting bar is fixed to a teeth to be treated. The supporting bar extends toward the implant member so as to be brought into contact with the implant. As the implant member serves as a stopper against the supporting bar, further unnecessary movement of the tooth is prevented (see Bousquet, Bousquet, Mauran, and parguel, Vol. XXX No. 5).

As described above, conventionally, the orthodontic treatment has been mainly conducted by a relative movement between teeth. In this treatment, tooth to be treated is moved to a desired position using another tooth (for example, a first molar tooth) as an anchorage. There is a possibility that the tooth used as an anchorage itself is moved from its correct position. Accordingly, complicated processes are required. For example, the tooth used as an anchorage is returned to its original correct position after the orthodontic treatment is completed, or the tooth used as an anchorage is connected to the other tooth before starting the orthodontic treatment in order to keep it to its correct position. Such an orthodontic treatment requires long time and is painful for a patient.

For a patient having a narrow dental arch, a treatment for expanding the dental arch is conducted. In this treatment, a rapid expansion appliance is adopted to rapidly expand the median palatine suture of the upper jaw.

FIG. 34 is a diagram for illustrating an orthodontic treatment using a rapid expansion appliance 40 and a pair of straps 40. One end of each strap 42 is fitted to the side teeth, and the other end thereof is connected to a rapid expansion appliance 40. The rapid expansion appliance 40 has an expansion screw. Turning the expansion screw applies a pushing force to the teeth toward both buccal sides, so that the median palatine suture 41 is expanded in a direction shown by arrows G.

The method using the rapid expansion appliance has a problem. In the treatment, a pushing force is applied to the teeth, and the pushed teeth are inclined toward buccal sides. As a result, the alignment of the teeth is disturbed.

The present invention was made to solve the above-described problems, and the objective thereof is to provide a supporting body for use in an orthodontic appliance. The supporting body is implanted in a maxilla and/or mandibula (or simply referred to as a jaw bone) to be used as an anchorage for applying a force to a tooth to be treated without adversely affecting the other correctly-positioned teeth. The treatment using the supporting body of the present invention requires no complicated processes.

Another objective of the present invention is to provide a supporting body for use in an orthodontic appliance which expands a median palatine suture without imposing unnecessary force to teeth.

Still another objective of the present invention is to provide an orthodontic method using the supporting body of the present invention.

SUMMARY OF THE INVENTION

The fulfill the above objects according to the present invention, a supporting body for use in an orthodontic appliance includes an implant member having a maximum dimension in its cross section of 2 mm or less for being implanted in a jaw bone, and an exposed member forming one end of the supporting body to be exposed to inside of mouth, and the exposed member includes an extended arm wherein the arm is formed with a hook (hereinafter, referred to as the first invention.).

In another aspect of the present invention, a supporting body for use in an orthodontic appliance includes an implant member to pierce a jaw bone, and an exposed member provided on opposite sides of the implant member to be exposed towards the interior of the mouth, and the exposed member has a hook via or without an arm (hereinafter, referred to as the second invention).

In still another aspect of the present invention, an orthodontic method includes a step of implanting a supporting body in a jaw bone, and a step of applying a force to a tooth to be treated thereby moving it to a desired position (hereinafter, referred to as the third invention.).

The above and other objects, features and advantages of the present invention will become more apparent upon reading of the following detailed description and drawings.

BRIEF DESCRIPTION OF THE DRAWINGS

FIG. 13 is a diagram for illustrating an orthodontic treatment 3 using the supporting body of the present invention;

FIG. 14 is a diagram showing a supporting body fur use in an orthodontic appliance according to Example 7 of the present invention;

DESCRIPTION OF THE PREFERRED EMBODIMENTS

In the orthodontic treatment of a tooth without using another tooth as an anchorage, a small-sized implant member is implanted in a maxilla and/or mandibula (or referred to as a jaw bone) through alveolus. At the same time, a bracket (or a lingual button) is fixedly attached onto the surface of the tooth to be treated. Then, the implant and the brackets are connected to each other by a member such as a resin chain and a spring. This method does not use another tooth as an anchorage, so that a treatment can be conducted without adversely affecting other correctly-positioned teeth. It should be noted that each one of bracket and the lingual button is also referred to as a fixing member in this specification.

However, there are some cases where complicated processes are required as described below.

Figure 32:
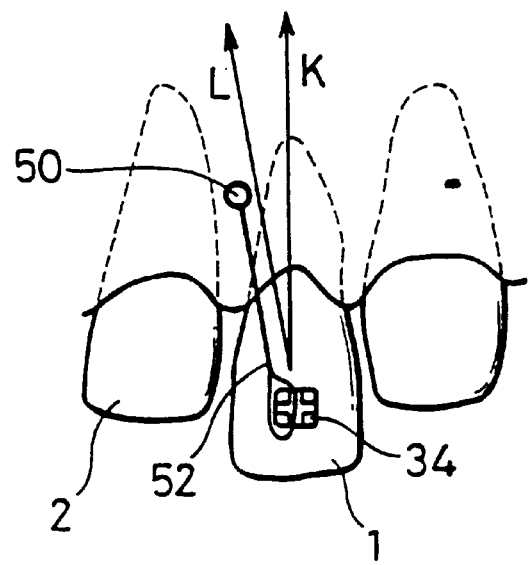
FIG. 32 is a front view for illustrating a treatment in which pressure is applied to an anterior tooth of an upper jaw.

FIG. 32 is a front view for illustrating a treatment in which a front tooth of upper jaw is pulled toward alveolus. An implant member 50 is implanted in a maxilla and/or mandibula through alveolus of the upper jaw. At the same time, a bracket 34 is fixedly attached onto the surface of the front tooth 1. The bracket 34 and the implant member 50 are connected to each other by a resin chain 52. The resin chain 52 pulls the front tooth 1 toward the alveolus via the bracket 34 using the implant 50 as an anchorage.

In this case, it is the most preferable that the front tooth 1 is pulled in the direction shown by an arrow K, that is, along the line longitudinally running through the center of the front tooth 1. In order to pull the front tooth 1 in the direction K, it is the most preferable that the implant member 50 is implanted on the line along the direction K.

However, as dental nerves and a root of the tooth 1 are present along the direction K, the implantation of the implant member 50 at a position along the direction K may possibly damage the dental nerves or the tooth root. In addition, when the front tooth 1 is to be moved along the direction K, the presence of the implant member 50 along the direction K may be an obstacle of the movement of the front tooth 1.

In the actual treatment, as shown in FIG. 32, the implant 50 is implanted in a maxilla and/or mandibula through the alveolus at a position between the front teeth 1 and 2. In this case, however, the front tooth 1 is pulled toward the direction of L, that is, along the line out of the longitudinally center of the front tooth 1. Therefore, the front tooth 1 is likely to be inclined. In order to prevent the front tooth 1 from being inclined, the front tooth 1 is connected to another tooth as a stopper. As a result, complicated processes are additionally required in the treatment.

When the tooth to be treated is pulled toward alveolus, the pulled tooth vigorously resists against the pulling force. Therefore, when an orthodontic treatment is conducted using a relative movement between teeth such as described above, the resisting force moves the tooth used as a stopper from its correct position.

Figure 31:
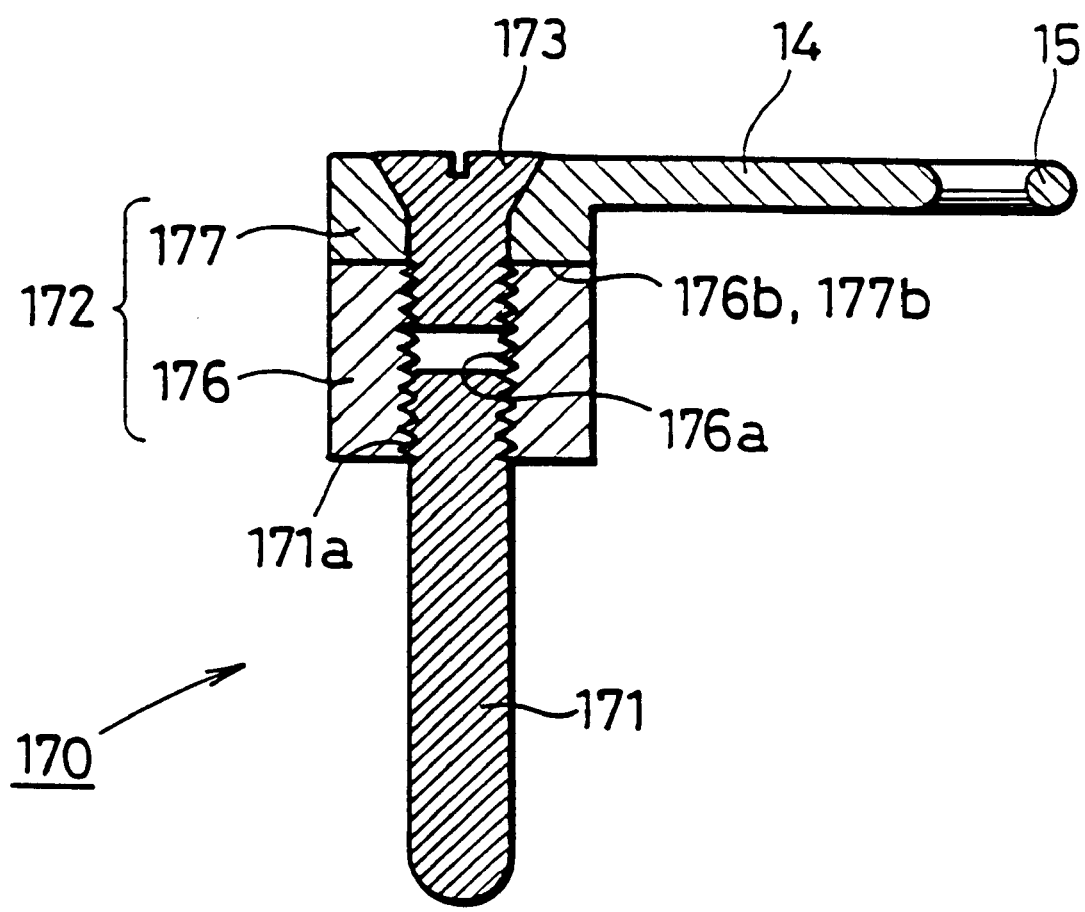
FIG. 31 is a longitudinal sectional view showing a supporting body of a supporting body for use in an orthodontic appliance according to Example 17 of the present invention.
Figure 33:
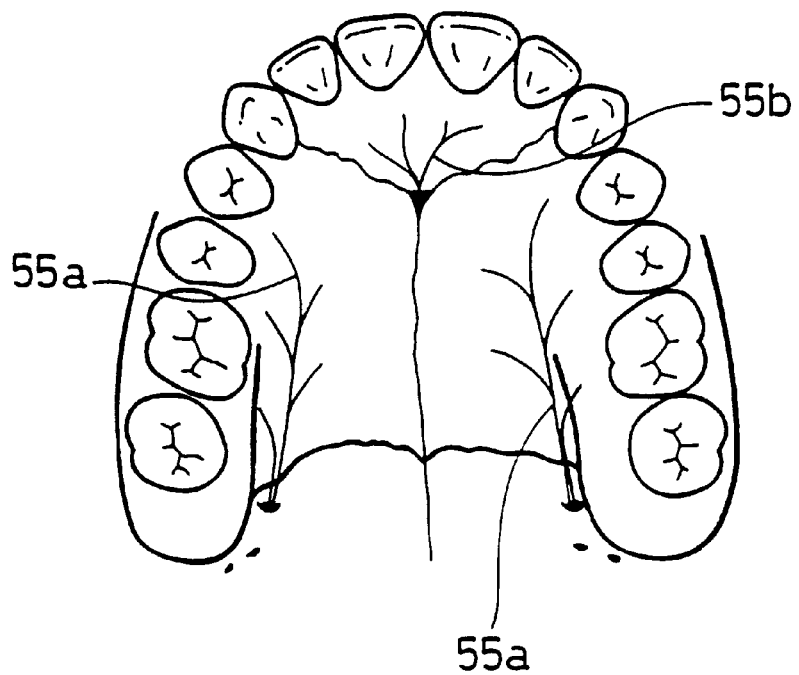
FIG. 33 is a diagram showing nerves of an upper jaw.
Figure 34:
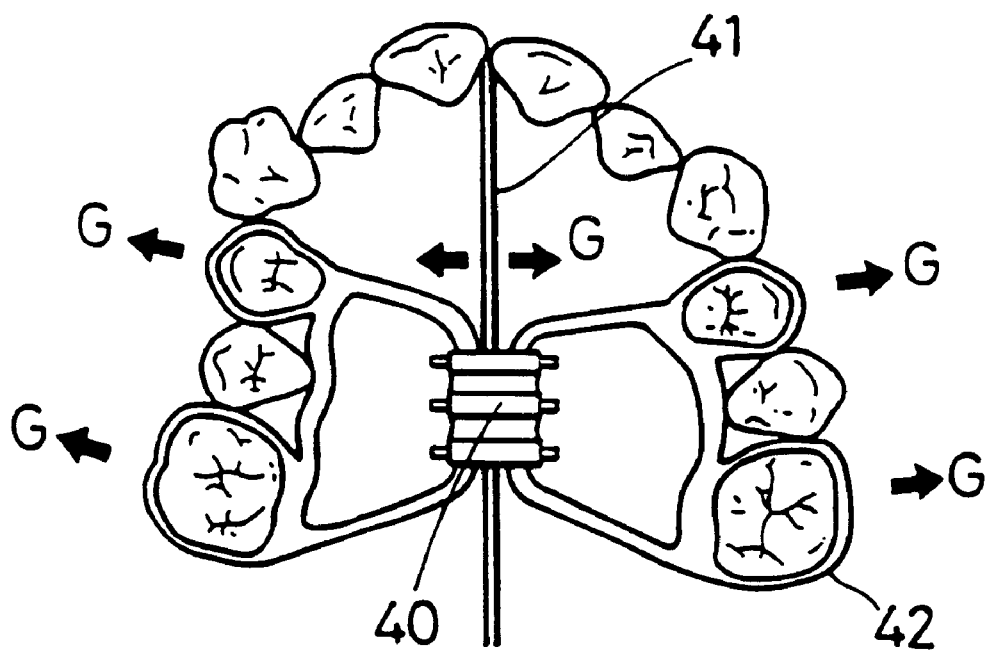
FIG. 34 is a diagram for illustrating a conventional treatment using a rapid expansion appliance.

FIG. 33 is a diagram showing main nerves which are present in the upper jaw. As shown in FIG. 31, the upper jaw has the greater palatine nerves 55a and the nasopalatine nerves 55b.

Other than the nerves shown in FIG. 33, there are various nerves in maxilla and/or mandibula. An implant member is required to be implanted while avoiding the nerves, and therefore, there are many cases where the implantation site is limited to a very small region. As a result, complicated processes are additionally required in the treatment.

Using the supporting body of the present invention, the application of the force to the tooth to be treated can be conducted from the most preferable position even if its implantation site is limited to a very small region.

In the first invention, a supporting body for use in an orthodontic appliance includes an implant member having a diameter of 2 mm or less for being implanted in a maxilla and/or mandibula and an exposed member forming one end of the supporting body to be exposed to inside of mouth, and the exposed member includes an extended arm and the arm is formed with a hook.

In an orthodontic treatment, the supporting body is implanted in the maxilla and/or mandibula at a position other than those having nerves in such a manner that the hook formed in the arm is located at a desired position. At the same time, a bracket and the like (hereinafter also referred to as a fixing member) is attached to the surface of the tooth to be treated. The bracket and the hook are connected to each other by a resin chain, a metallic coil spring and the like, so that a force required for treatment is applied to the tooth to be treated. This force moves the tooth to a desired position using the hook as an anchorage.

Due to the presence of the arm, the hook is located at a position apart from the implantation site of the implant member. Therefore, while implanting the implant member at a position having no nerves in the maxilla and/or mandibula, the hook can be located at a position which is the most preferable for the application of the force. In addition, by properly selecting the orientation and the length of the arm, the most preferable distance between the implantation site and the hook and the most preferable orientation of the hook can be obtained.

As a result, the tooth to be treated can be moved to a desired position with simple processes and only a short period of time.

A supporting body of the present invention has an implant member with a diameter of 2 mm or less. Due to such a small diameter, the implant member is easily implanted in the maxilla and/or the mandibula while avoiding nerves, for example, at an interval of about 3 mm between nerves with little harmful influence to human body.

Preferably, the implant member has a diameter of 1.5 mm or less, and more preferably 1 mm or less. This is because, as described above, an implant member with a small diameter can be implanted in the maxilla and/or mandibula while avoiding nerves with less harmful influence to human body. The lower limit of the diameter is 0.5 mm, because an implant member with a diameter smaller than this may not withstand a force applied for treatment, and may slip off the implantation site.

A supporting body is required to withstand a force of 100 to 300 g normally, and at most, 1 kg. According to the present invention, it has been found that an implant member with a diameter of 2 mm or less, or even 1 mm or less is sufficient to be used in an orthodontic treatment.

The length of the implant member is selected in accordance with the thickness of the maxilla and/or mandibula of the implantation site. Preferably, the implant member has a length of 5 to 15 mm. With too short a length, an implant may not withstand a force applied thereto for a treatment. With too large length, an implant may give a harmful effect on maxilla and/or mandibula.

Preferably, the supporting body is made of titanium or a titanium alloy, because titanium or titanium alloy has excellent bio-compatibility.

The arm may have not only one hook but also two or more hooks.

According to the present invention, the implant member and the exposed member are independently formed with each other, and the exposed member is mountable to the implant member to form a one piece unit when in use. The entire exposed member is essentially exposed to the inside of mouth; however, a part of the exposed member may be buried in gingiva. In addition, the entire implant member is essentially implanted in the maxilla and/or mandibula; however, the entire implant member is not necessarily implanted in the maxilla and/or mandibula.

As described above, the exposed member and the implant member are independently formed with each other and the exposed member is mountable to the implant member. Accordingly, when it becomes necessary to change a position of hook after implanting the implant member in the maxilla and/or mandibula, the exposed member is reset in such a manner that the hook is relocated at a desired position. Moreover, if no treatment is conducted after the implantation of the implant member until it firmly coalesces in the maxilla and/or mandibula, the exposed member is not mounted. When the implant member firmly coalesces in the maxilla and/or mandibula and the treatment is restarted, the exposed member is mounted to the implant member. During the period where the exposed member is not mounted to the implant member, the lip, bucca, or tongue will have decreased sense of discomfort.

Preferably, the supporting body has a screw member for screw connecting the implant member and the exposed member.

Furthermore, the angle formed between the axial centers of the arm and the implant member (hereinafter, referred to as an upward angle in some cases) is set in a range between 90 degrees to 180 degrees, and more preferably in a range between 90 degrees to 160 degrees.

If the arm forms an upward angle with respect to the implant member implanted in the maxilla and/or mandibula as described above, the hook formed in the arm can be located apart from the alveolus. With this arrangement, when the hook and the bracket are connected to each other by a resin chain and the like, the resin chain can be kept apart from the alveolus. This is advantageous because it is possible to prevent the alveolus from being inflamed by the contact with the resin chain and the like. However, too large a distance between the bracket and the hook may give a sense of discomfort to the lip, bucca, or tongue. Therefore, the upward angle is optimally set to such a degree that the lip, bucca, or tongue suffer at a minimum an uncomfortable feeling.

According to the present invention, the exposed member is formed with a polygonal shape or radial teeth engagement shape recess and one end of the implant member is formed with a corresponding polygonal shape or radial teeth engagement shape projection fitting to the polygonal shape or radial teeth engagement recess, whereby the arm is selectably oriented in a plane perpendicular to the axial direction of the implant member (hereinafter, referred to as an arm direction on the horizontal surface in some cases).

By optimally selecting the arm direction on the horizontal surface, a length, and the upward direction of the arm, the hook is located at the most preferable position to be an anchorage for the application of force to the tooth to be treated.

In the present invention, preferably, the exposed member has a tapered surface with respect to the insertion direction (or a longitudinal center of the supporting body) and the implant member has a corresponding tapered surface, whereby the exposed member is firmly fitted to the implant member Furthermore, in the present invention, the supporting body has a plurality of arms formed with a hook. In this case, two or more hooks oriented in different directions from each other are obtainable at one implantation site.

The arm may be made of a plate spring. In this case, a restoring force (an elastic force) generated by the arm is applied to a tooth to be treated, whereby the tooth is moved to a desired position.

Note that the cross sectional shape of the implant member is not necessarily limited to a circular shape but it could be an oval shape and a polygonal shape. Thus if the cross sectional shape is other than a circular, the maximum dimension of the cross section of the implant member is still preferably 2 mm or less than 2 mm.

Next, the second invention will be described.

The supporting body of the second invention includes an implant member to pierce the maxilla and/or mandibula, and an exposed member provided on opposite sides of the implant member to be exposed to inside a mouth. Each exposed member has a hook on its end with or without an arm.

Each hook is connected to brackets attached to a tooth to be treated by a resin chain and the like to apply a force to the tooth, and the force moves the tooth to a desired position.

According to the second invention, there are a variety of embodiments of the supporting body. Examples thereof include a supporting body having exposed members provided on its opposite ends each of which has an arm formed with a hook, a supporting body having exposed members on its opposite ends only one of which has an arm formed with a hook, and a supporting body having exposed members on its opposite ends neither of which has an arm and hooks which are directly formed. If a supporting body has an arm formed with a hook, the hook can be located at a desired position by orienting the arm in a desired direction, even though an implantation site is limited to a small region.

The implant member preferably has a diameter of 2 mm or less, and more preferably 1.5 mm or less, and the most preferably 1.0 mm or less. This is because, as described above, an implant member with small diameter can be implanted in the maxilla and/or mandibula while avoiding nerves with less harmful influence to human body. The lower limit of the diameter is 0.5 mm, because an implant member with a diameter smaller than this may not withstand a force applied for treatment, and may slip off the implantation site.

Preferably, the implant member and the exposed member are independently formed of each other and the exposed member is mountable to the implant member to form a one piece unit when in use. As is the case of the first invention, the exposed member is not mounted to the implant member until it is needed or can be replaced with another one.

The supporting body may include a screw member for screw connecting the implant member and the exposed member. In addition, the exposed member may have a tapered recess and the implant member has a corresponding tapered projection, whereby the exposed member is firmly fitted to the implant member.

The angle formed between the axial centers of the arm and the implant member (hereinafter, referred to as an upward angle) is set in a range between 90 degrees to 180 degrees, and more preferably in a range between 90 degrees to 160 degrees. If the arm forms the upward angle with respect to the implant member implanted in the maxilla and/or mandibula, the hook and the resin chain can be kept apart from the alveolus.

The exposed member is formed with a polygonal shape or teeth engagement recess and one end of the implant member is formed with a corresponding polygonal shape or teeth engagement projection fitting to the polygonal shape recess, whereby the arm is selectably oriented in a plane perpendicular to the axial direction of the implant member (hereinafter, referred to as a horizontal direction of the arm).

The supporting body has a plurality of arms formed with a hook. In this case, a plurality of hooks oriented in different directions from each other are obtainable from one exposed member.

One arm may have a plurality of hooks.

The arm may be made of a plate spring. In such a case, the restoring force (an elastic force) generated by the arm is applied to a tooth to be treated, whereby the tooth is moved to a desired position.

Note that the cross sectional shape of the implant member is not necessarily limited to a circular shape but it could be an oval shape and a some polygonal shape. So, if the cross sectional shape is other than a circular, then still the maximum dimension of the cross section of the implant member is preferably 2 mm or less than 2 mm.

Next, the third invention will be described. The third invention relates to a method for conducting an orthodontic treatment using the supporting body of the present invention.

The third invention is further categorized into three orthodontic methods. The first method uses the supporting body of the first invention, and includes a step of implanting the implant member in the maxilla and/or mandibula, a step of attaching a bracket (also referred to as a fixing member) and/or a lingual button and the like (also referred to as a fixing member) to a tooth to be treated, a step of connecting the bracket and/or the lingual button and the hook by an elastic member, and a step of applying an elastic force generated by the elastic member to the tooth.

Using the hook as an anchorage, a force required for treatment is applied to the tooth to be treated, so that the tooth is moved to a desired position.

The second method uses a supporting body having an implant member and an arm made of a plate spring formed with a hook. The method includes a step of implanting the implant member in the maxilla and/or mandibula, a step of attaching a bracket and/or a lingual button to a tooth to be treated, a step of connecting the bracket and/or the lingual button and the hook by an elastic member, and a step of applying an elastic force generated by the elastic member to the tooth.

In this manner, a restoring force (an elastic force) generated by the arm is applied to the tooth to be treated, whereby the tooth is moved to a desired position.

The third method uses a supporting body of the second invention including an implant member to pierce the maxilla and/or mandibula and a hook provided at its opposite ends with or without arm. The third method includes a step of piercing the implant member in the maxilla and/or mandibula, a step of attaching a bracket and/or lingual button to a tooth to be treated, a step of connecting the bracket and/or lingual button and the hook by an elastic member, and a step of applying an elastic force generated by the elastic member to the tooth.

In this manner, the force required for treatment is applied to the tooth to be treated, whereby the tooth is moved to a desired position.

The hook may be any member selected from those normally used in an orthodontic treatment, for example, brackets and lingual buttons. Examples of an elastic member include resin chains, coil springs, rubber hooks, and the like.

DESCRIPTION OF THE SUPPORTING BODY

EXAMPLE 1

Figure 1C:
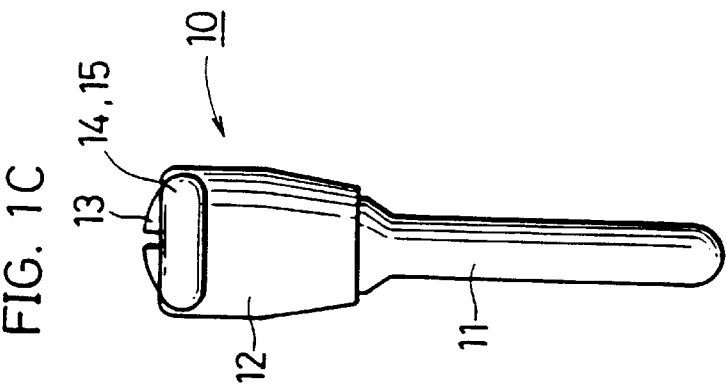
FIGS. 1A, 1B, and 1C are diagrams showing a supporting body for use in an orthodontic appliance according to Example 1 of the present invention.
Figure 1B:
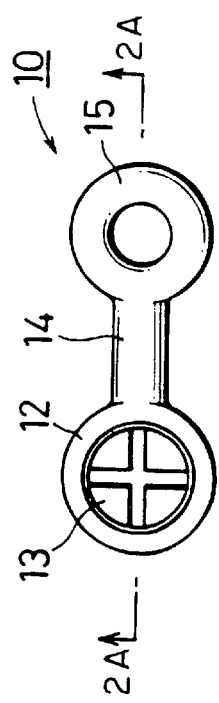
Figure 1A:
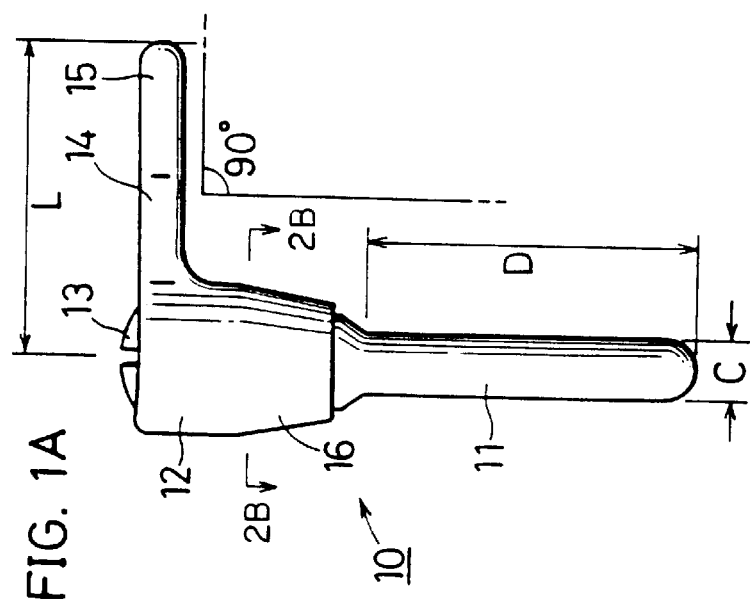
Figure 2A:
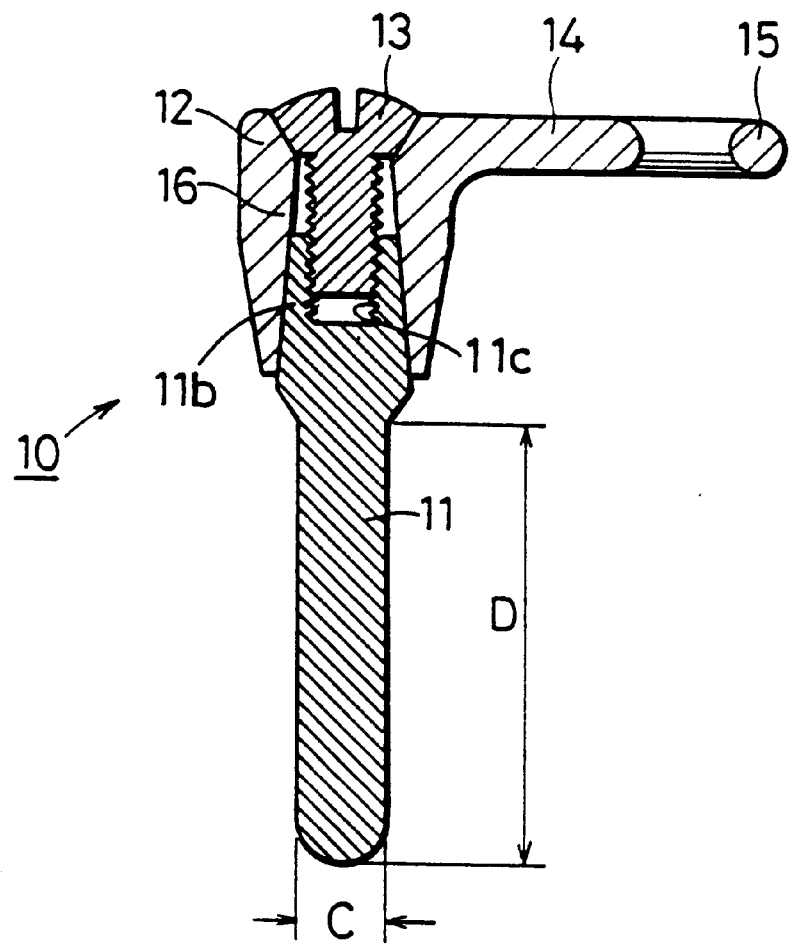
FIG. 2A is a cross-sectional view showing a supporting body for used in an orthodontic appliance taken along a line 2A—2A of FIG. 1.
Figure 2B:
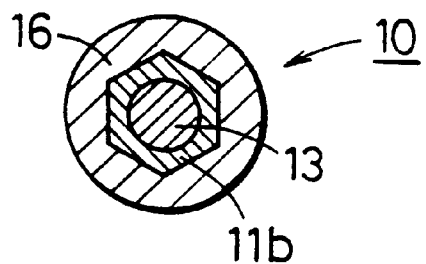
FIG. 2B is a cross-sectional view showing a supporting body for use in an orthodontic appliance taken along a line 2B—2B of FIG. 1.

FIGS. 1 and 2 are diagrams illustrating a supporting body according to Example 1 of the present invention. FIG. 1A is a front view thereof. FIG. 1B is a top view thereof. FIG. 1C is a right side view thereof. FIG. 2A is a cross-sectional view showing a supporting body of FIG. 1B along a line 2A—2A. FIG. 2B is a cross-sectional view showing a supporting body of FIG. 1A along a line 2B—2B.

A supporting body 10 includes an implant member 11, an abutment (an exposed member) 12, and a male screw 13 for fixing the implant member 11 and the abutment 12 to each other. In Example 1, the implant member 11 has a diameter C of about 1 mm, and a length D of about 5 mm.

The abutment 12 has an arm 14 to be extended inside a mouth when in use, and the arm is formed with a hook 15 on its end. As shown in FIG. 1A, the angle formed between the axial centers of the arm 14 and the implant member 11 is 90 degrees. The arm 14 has a length L of about 4 mm.

The implant 11 has a projection 11b on its head portion, which is tapered with decreasing diameter toward its top end. On the other hand, the abutment 12 has a recess 16 which is tapered in correspondence with the shape of the projection 11b with a diameter increased toward its bottom. The projection 11b is formed with a female screw hole 11c so as to fit a male screw 13 therein. The abutment 12 and the implant member 11 are connected to each other by the projection 11b and the recess 16, and are further firmly fixed to each other by the male screw 13.

Due to the tapered shapes of the projection 11b and the recess 16 corresponding to each other, the abutment 12 and the implant 11 are firmly fitted to each other when tightened by the screw 13.

In addition, due to the tapered shapes, there is no need to match the length of the length of the male screw 13 to the depth of the female hole 11c. It is only required that the female screw hole 11c is required to have a depth larger than the length of the male screw 13. The formation of such a structure is easy. Contrary to this, if the screw connection is completed only when the bottom end of the male screw 13 is brought into contact between the bottom of the female screw hole 11c, it is required that the length of the male screw 13 be identical to the depth of the female screw hole 11c. The formation of such a structure requires high level of processing technique In addition, as shown in FIG. 2B, the projection 11b of the implant member 11 is hexagonal-shaped and the recess 16 of the abutment 12 is hexagonal-shaped as well, and they are fittingly engageable to each other.

In this case, the fitting of the abutment 12 with respect to the implant member 11 can be changed by 60 degrees. Accordingly, the horizontal direction along which the arm 14 extends can be changed by 60 degrees, so that the hook 15 provided on its end can be located at a desired position.

EXAMPLE 2

Figure 3B:
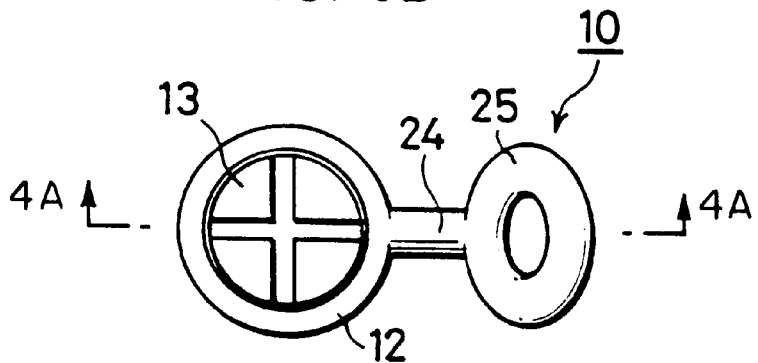
FIG. 3 is a diagram showing a supporting body for use in an orthodontic appliance according to Example 2 of the present invention.
Figure 3A:
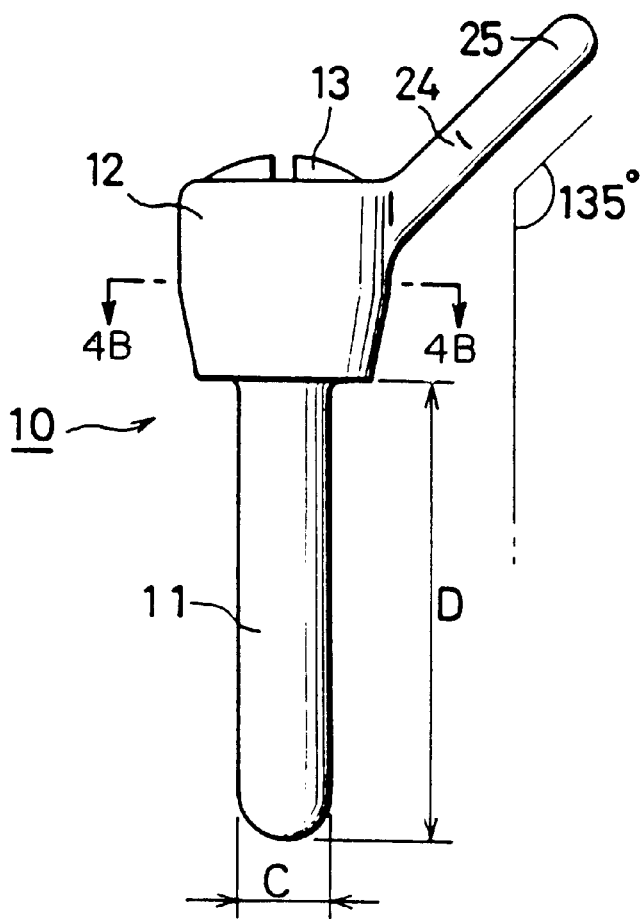
Figure 3C:
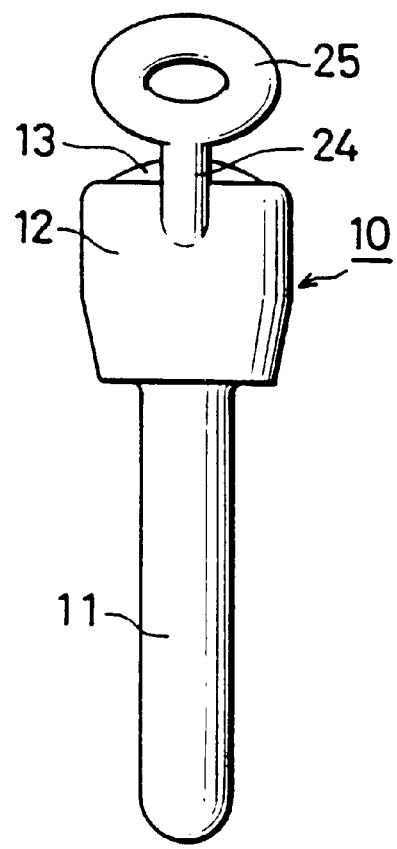
Figure 4A:
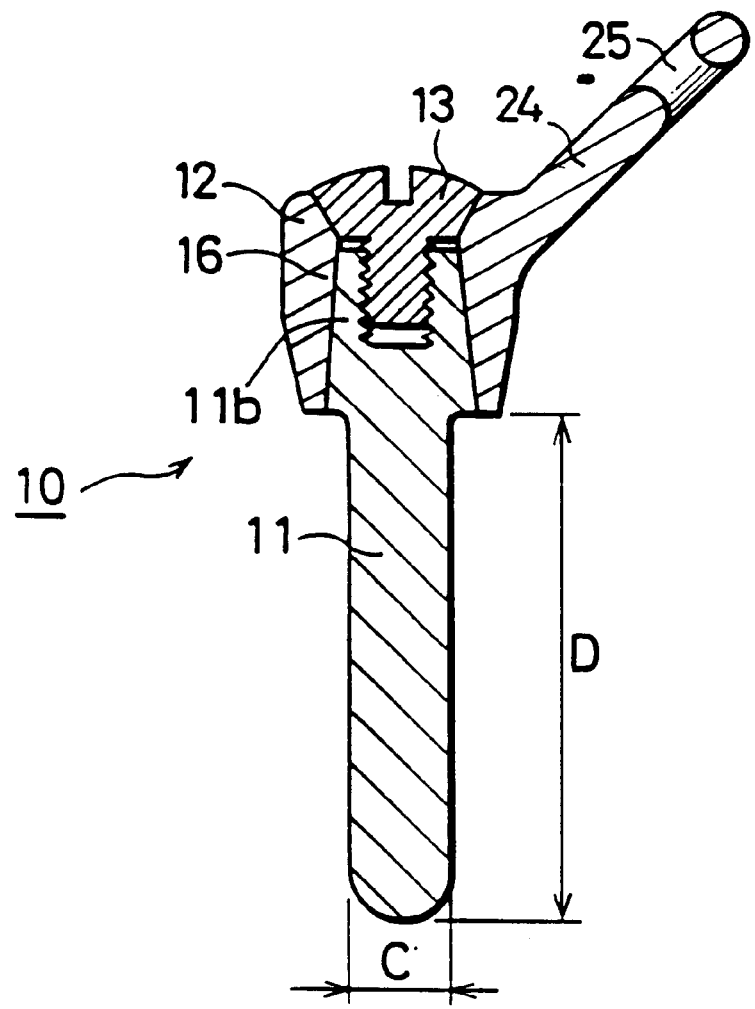
FIG. 4A is a cross-sectional view showing a supporting body for used in an orthodontic appliance taken along a line 4A—4A in FIG. 3B.
Figure 4B:
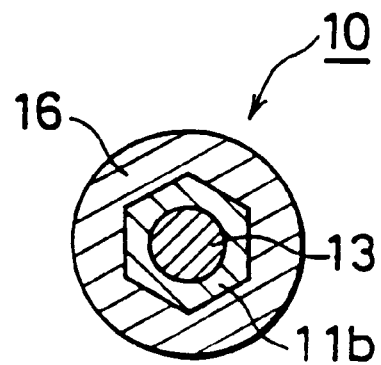
FIG. 4B is a cross-sectional view showing a supporting body for used in an orthodontic taken along a line 4B—4B of FIG. 3A.

FIG. 3 and 4 are diagrams showing a supporting body according to Example 2 of the present invention. FIG. 3A is a front view thereof. FIG. 3B is a top view thereof. FIG. 3C is a right side view thereof. FIG. 4A is a cross-sectional view showing a supporting body taken along a line 4A—4A of FIG. 3B. FIG. 4B is a cross-sectional view showing a supporting body taken along a line 4B–4B of FIG. 3A.

In Example 2, used is a supporting body having a structure identical to the supporting body 10 used in Example 1 except that the angle formed between the axial centers of the arm 24 and the implant member 11 is set 135 degrees, (see FIG. 3A), and the arm 24 has a height smaller than that of the arm 14 of Example 1. The constituent elements having structures identical to those of Example 1 have the same reference numerals, and the description thereof will be omitted.

When the axial centers of the arm 24 and the implant member 11 form an obtuse angle with each other, neither the hook 25 nor the resin chain is brought into contact with alveolus. In addition, such an obtuse angle produces a wide space between the hook 25 and the alveolus, so that the attachment of the chain to the hook 25 is easy.

EXAMPLES 3 to 6

Figure 5:
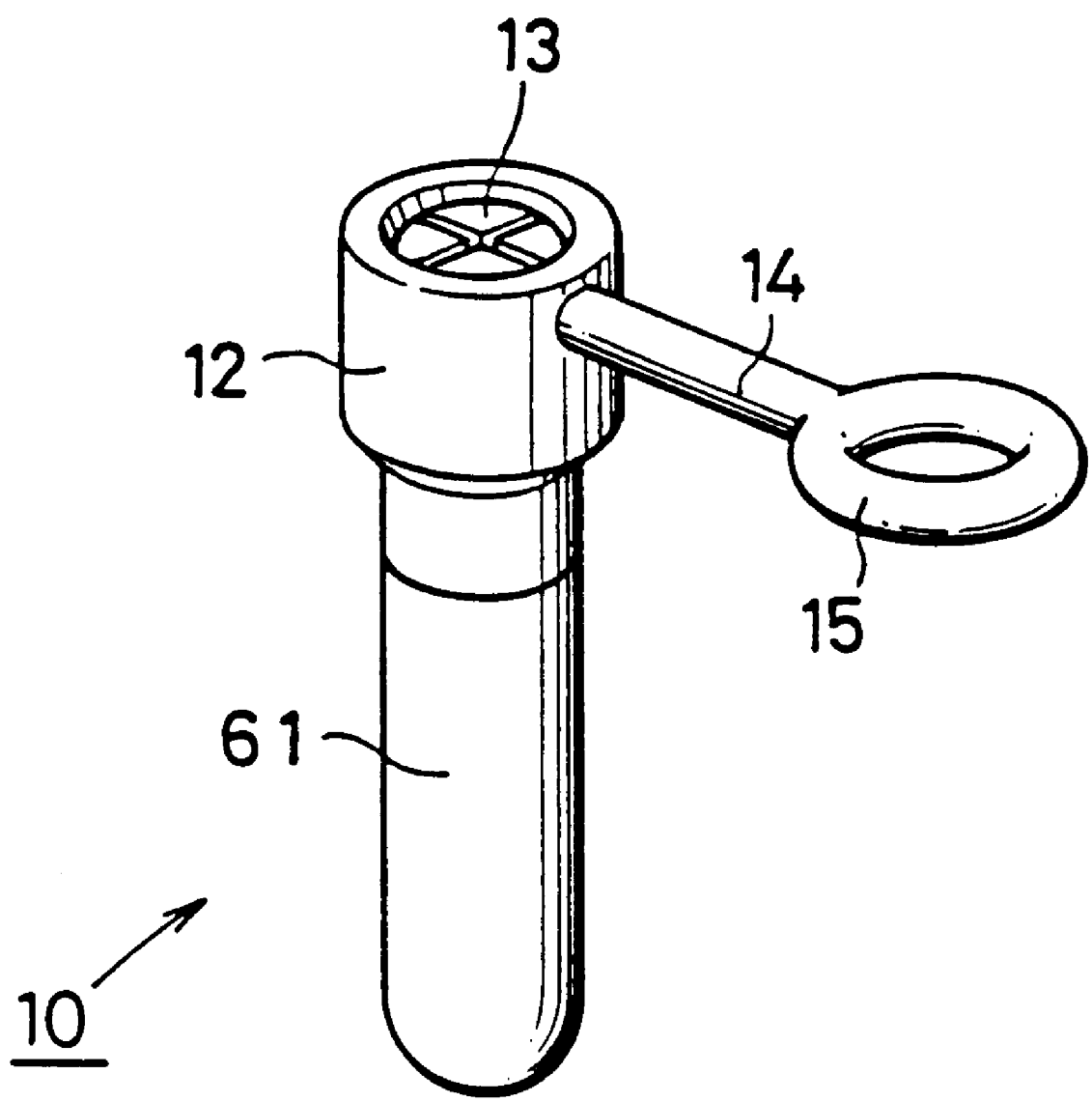
FIG. 5 is a supporting body for use in an orthodontic appliance according to Example 3 of the present invention.
Figure 6:
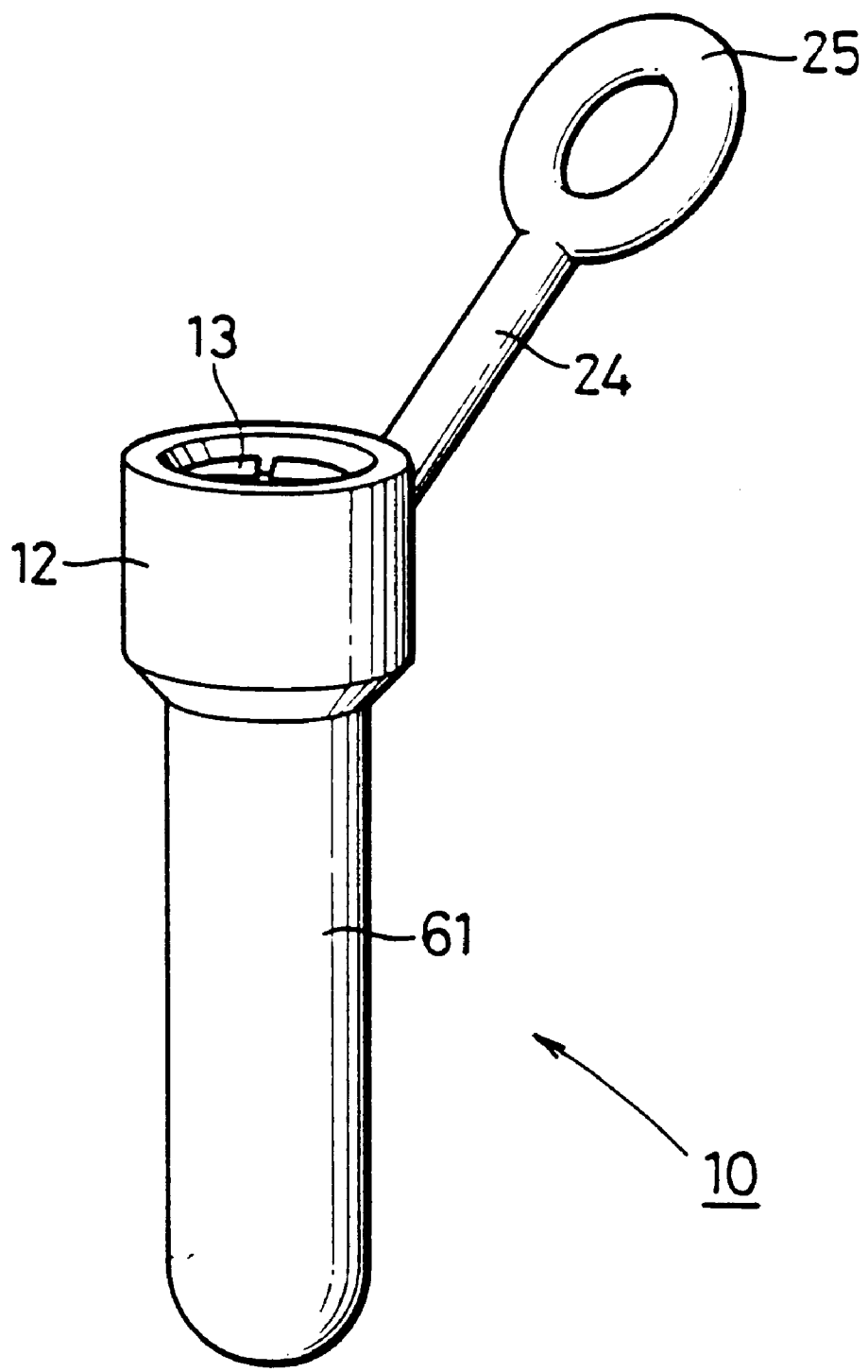
FIG. 6 is a perspective view showing a supporting body for used in an orthodontic appliance according to Example 4 of the present invention.
Figure 7:
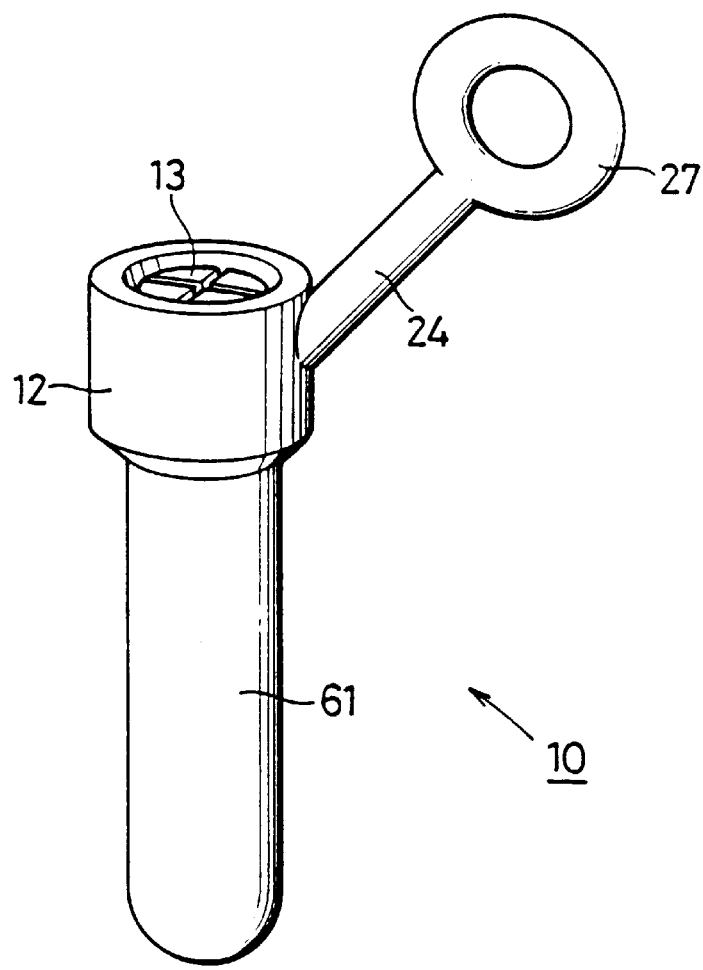
FIG. 7 is a perspective view showing a supporting body for use in an orthodontic appliance according to Example 5 of the present invention.
Figure 8:
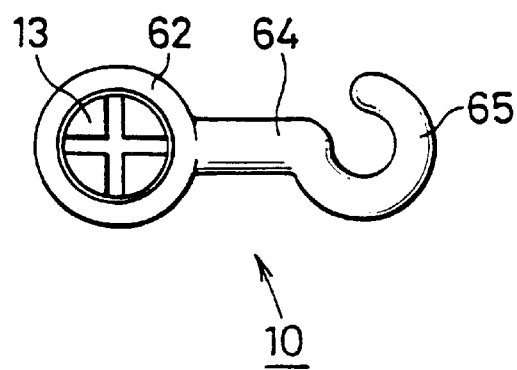
FIG. 8 is a perspective view showing a supporting body for use in an orthodontic appliance according to Example 6 of the present invention.

FIGS. 5 to 7 are perspective diagrams showing a supporting body 10 according to Examples 3 to 5 of the present invention. FIGS. 5, 6, and 7 are diagrams respectively showing a supporting body according to Examples 3, 4, and 5 of the present invention. FIG. 8 is a top view showing a supporting body 10 according to Example 6 of the present invention.

In Examples 3 to 5, an implant 61 has a diameter of 1.5 mm, which is larger than that of Examples 1 and 2. While the hook 25 in Examples 1 to 4 has an opening opened in a direction parallel to the top of the abutment 12, the hook 27 in Example 5 has an opening opened in a direction perpendicular to the top of the abutment 12 (see FIG. 7). In Example 6 an opened hook 65 is provided at the leading end of an arm 64 extending from an abutment 62 (see FIG. 8), so that a chain can be easily set to the hook 65. In Examples 3 to 6, the constituent elements having structured identical to those of Examples 1 to 4 have the same reference numerals, and the description thereof will be omitted.

EXAMPLE 7

FIG. 14 is a diagram showing a supporting body according to Example 7 of the present invention. FIG. 14A is a front view thereof. FIG. 14B is a top view thereof.

In Example 7, an abutment 72 has an arm 74 consisting of a plurality of rings. Each ring can be cut off so that the length of the arm 74 can be shortened. The ring located at the end of the arm 74 is used as a hook 75. With this structure, the length of the arm 74 can be adjusted even when the abutment 72 is fixed to the implant 11, so that the position of the hook 75 can be adjusted along the length of the arm.

In Example 7, the adjustment of the length of the arm is not limited to the above-described method; however, the arm may be slidable along its length direction thereby freely changing its length.

In addition, not only the hook 75 located at the end of the arm 74 but also any of rings forming the arm 74 can be used as a hook. Therefore, two or more hooks can be obtained from one supporting body.

EXAMPLES 8 and 9

Figure 15:
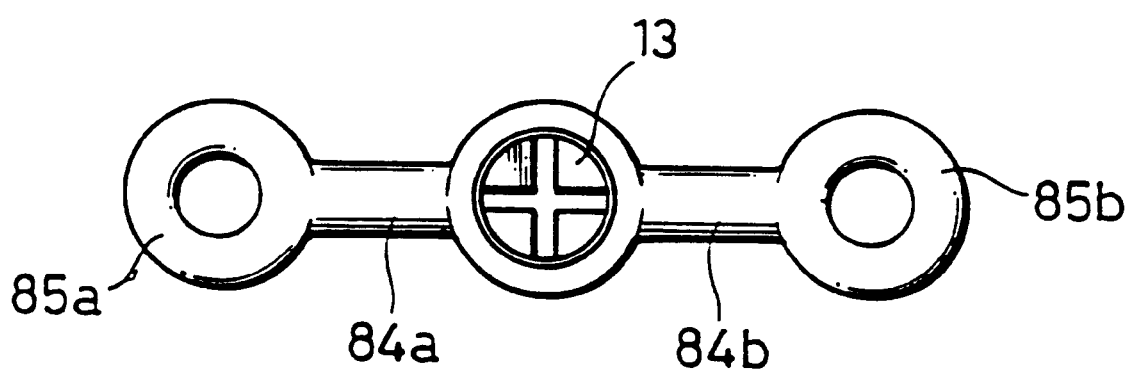
FIG. 15 is a top view showing a supporting body for use in an orthodontic appliance according to Example 8 of the present invention.
Figure 16:
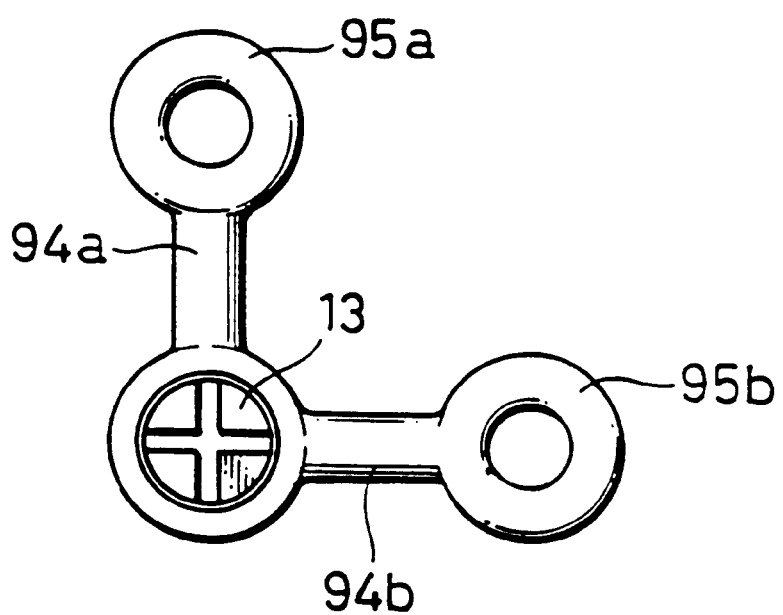
FIG. 16 is a top view showing a supporting body for use in an orthodontic appliance according to Example 9 of the present invention.

FIG. 15 is a top view showing a supporting body of Example 8 of the present invention. FIG. 16 is a top view showing a supporting body of Example 9 of the present invention.

In Example 8, a supporting body has two arms 84*a* and 84*b* each of which is formed with a hook 85*a* and 85*b* on its end. In Example 9, a supporting body has two arms 94*a* and 94*b* each of which is formed with a hook 95*a* and 95*b* on its end. In Example 8, the angle formed between the axial centers of the arm 84*a* and the arm 84*b* is 180 degrees. In Example 9, the angle between the axial centers of the arm 94*a* and the arm 94*b* is 90 degrees.

With this structures, two hooks oriented in different directions from each other can be obtained from one supporting body.

The angle formed between the axial centers of two arms is not limited to 180 degrees and 90 degrees, but may be other various degrees.

In addition, the supporting body of Examples 8 and 9 may have three or more arms formed with a hook on their respective ends. In this case, three or more hooks can be obtained from one supporting body.

EXAMPLE 10

Figure 17:
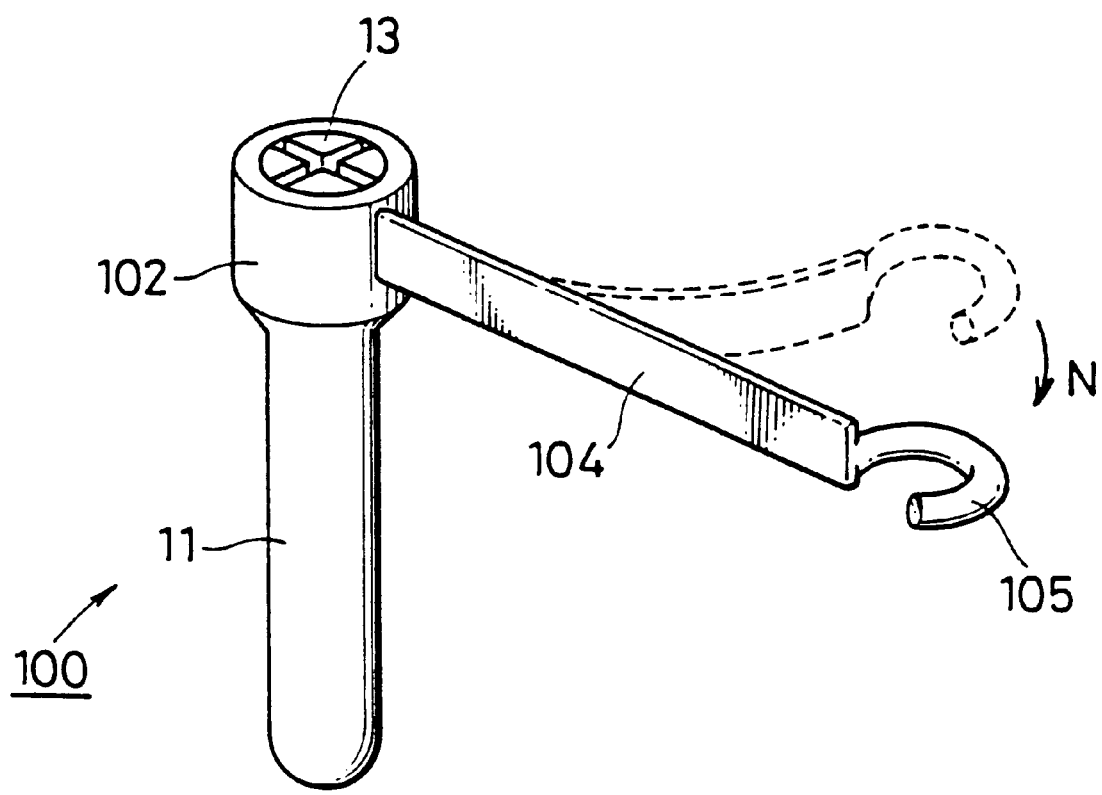
FIG. 17 is a diagram showing a supporting body for use in an orthodontic appliance according to Example 10 of the present invention.

FIG. 17 is a perspective view showing a supporting body according to Example 10 of the present invention.

In Example 10, an supporting body 100 includes an implant member 11 and an abutment (an exposed member) 102 having an arm 104 made of a plate spring formed with a hook 105 on its end.

The arm 104 made of a plate spring generates an elastic force, and the force is applied to the tooth to be treated, so that the tooth is moved to a desired position. For example, when the hook 105 is engaged to a tooth to be treated while curving the arm 104 as shown by a dashed line in FIG. 17. In this state, an elastic force is generated along a direction N, and the force is applied to the tooth. Accordingly, the tooth is moved to a desired position.

EXAMPLE 11

Figure 19B:
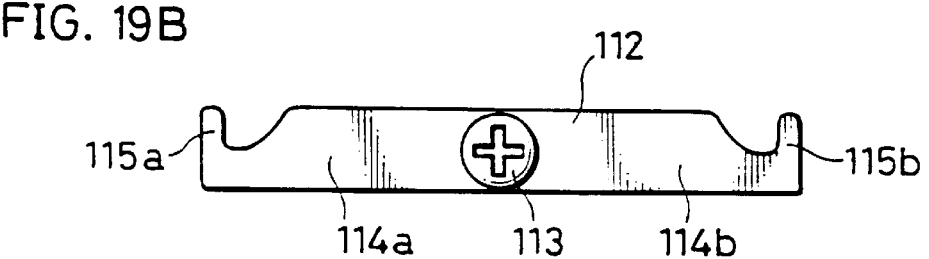
FIG. 19 is a diagram showing a supporting body for use in an orthodontic appliance according to Example 11 of the present invention.
Figure 19A:
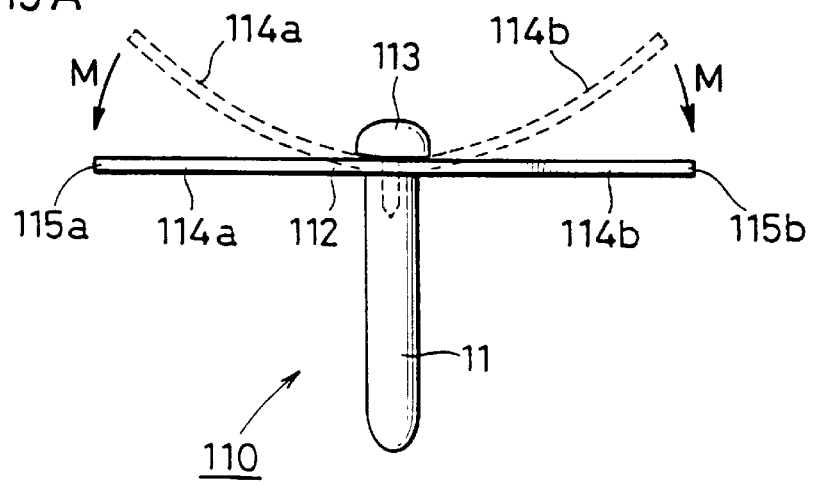

FIG. 19 is a diagram showing a supporting body according to Example 11 of the present invention. FIG. 19A is a front view thereof. FIG. 19B is a top view thereof.

In Example 11, a supporting body 110 includes an implant member 11 and an abutment (an exposed member) 112 having arms 114*a* and 114*b* made of a plate spring extending toward the opposed directions. The arms 114*a* and 114*b* are formed with hooks 115*a* and 115*b* on their respective ends. The abutment 112 is fixed to the implant 11 by a screw 113.

As is the case of Example 10, the arms 114*a* and 114*b* made of plate spring generates an elastic force, and the force is applied to a tooth to be treated, so that the tooth is moved to a desired position. For example, when the hooks 115*a* and 115*b* are engaged to a tooth to be treated while curving the arms 114*a* and 114*b* as shown by a dashed line in FIG. 19A. In this state, an elastic force is generated along a direction M, and the force is applied to the tooth. Accordingly, the tooth is moved to a desired position.

EXAMPLE 12

Figure 21:
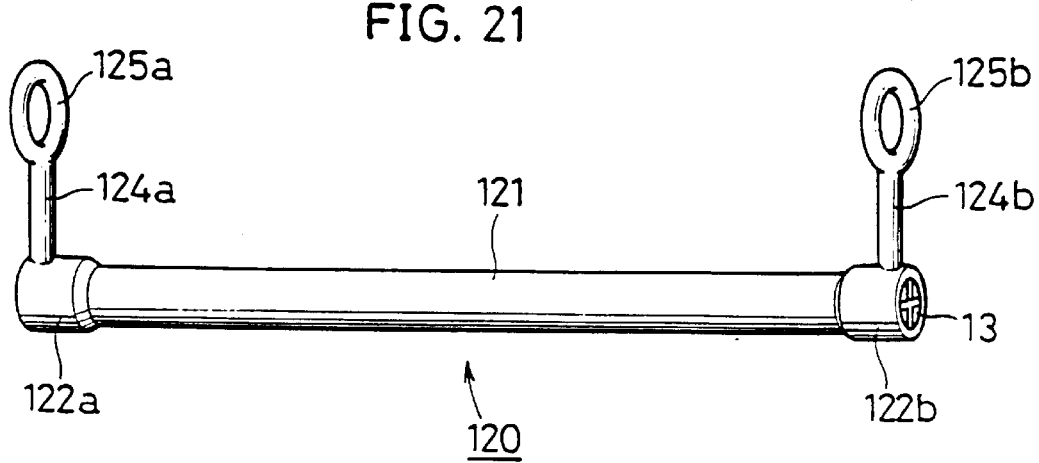
FIG. 21 is a perspective view showing a supporting body for use in an orthodontic appliance according to Example 12 of the present invention.

FIG. 21 is a perspective view showing a supporting body according to Example 12 of the present invention.

In Example 12, a supporting body 120 pierces maxilla and/or mandibula. The supporting body 120 includes an implant member 121 and abutments (exposed members) 122*a* and 122*b* firmly fixed on its both ends by screws 13. The abutments 122*a* and 122*b* has arms 124*a* and 124*b* respectively; each of arms is formed with hooks 125*a* and 125*b* respectively.

EXAMPLE 13

Figure 23:
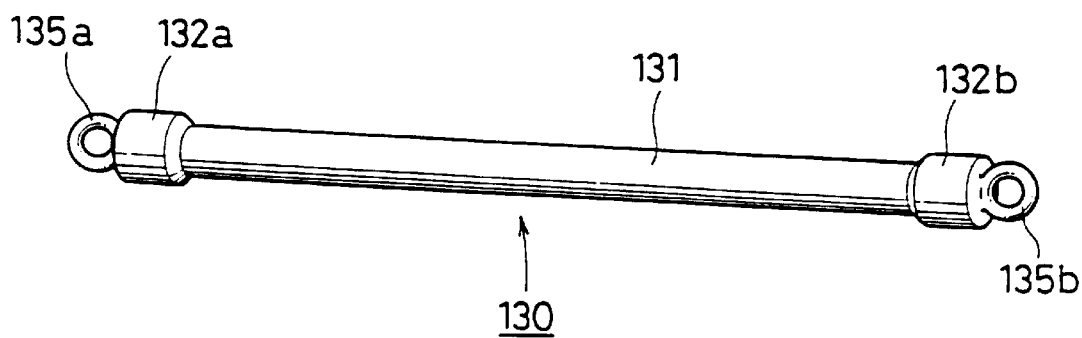
FIG. 23 is a perspective view showing a supporting body according to Example 13 of the present invention.

FIG. 23 is a diagram showing a supporting body according to Example 13 of the present invention.

In Example 13, as is the case of Example 12, a supporting body 130 includes an implant member 131 and abutments (exposed members) 132*a* and 132*b* on its both ends. The abutments 132*a* and 132*b* are formed with hooks 135*a* and 135*b*, respectively.

The abutments 132*a* and 132*b* have no arms. Therefore, the supporting body 130 of Example 13 is suitable to be used a treatment in which the abutments 132*a* and 132*b* of the supporting body 130 can be located at the most desirable position to be used as an anchorage for applying a force to the tooth via a resin chain and the like.

EXAMPLE 14

Figure 25A:
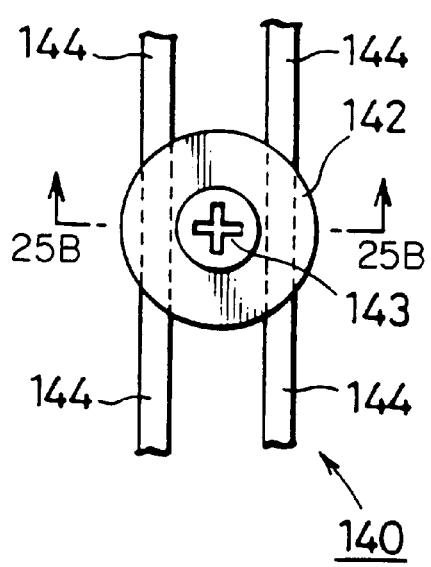
FIGS. 25A and 25B are diagrams showing a supporting body for use in an orthodontic appliance according to Example 14 of the present invention.
Figure 25B:
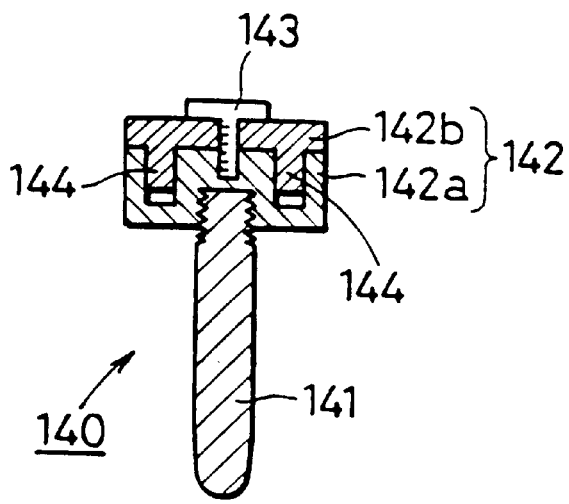

FIG. 25 is a diagram showing a supporting body according to Example 14 of the present invention. FIG. 25A is a top view thereof. FIG. 25B is a cross-sectional view showing a supporting body of FIG. 25A along a line 25B—25B.

A supporting body 140 includes an implant member 141 and an abutment (also referred to as an exposed member) 142. The abutment 142 consists of an upper member 142*b* having four arms 144 and a lower member 142*a* which is to be connected to an implant member 141. The upper member 142*b* and the lower member 142*a* are connected to each other by a screw 143.

EXAMPLE 15

Figure 28A:
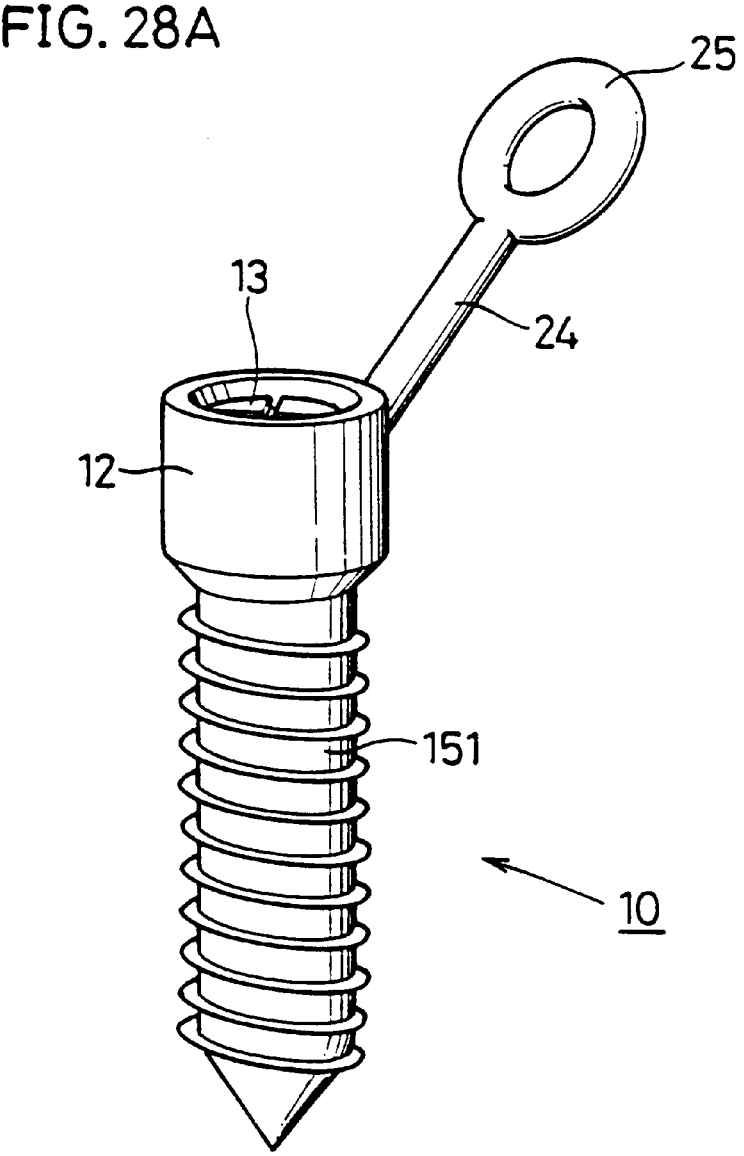
FIG. 28 is a diagram showing a supporting body for use in an orthodontic appliance according to Example 15 of the present invention.
Figure 28B:
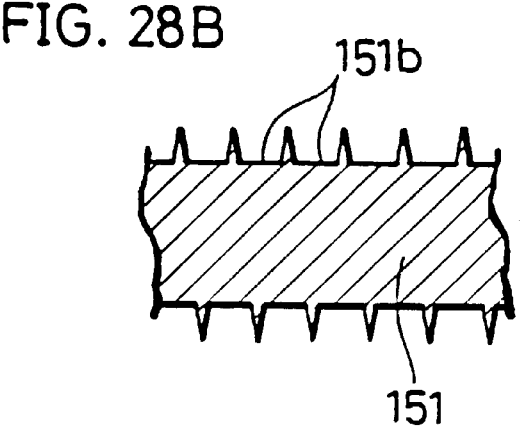

FIG. 28 is a diagram showing a supporting body according to Example 15 of the present invention. FIG. 28A is a perspective view thereof. FIG. 28B is a partially sectional view showing a part of an implant member 151 of the supporting body of FIG. 28A along its axial direction.

In Example 15, a supporting body 10 has a structure identical to that of Example 4 except that the implant member 151 has screw threads of the same height each other on its outer surface, so that the implant member 151 is in a form of male screw. Having a form of male screw, the implant member 151 can be firmly fixed to the maxilla and/or mandibula.

In Example 15, the surface of the implant member 151 is formed in such a manner that each screw thread has a sharp leading end, and the pitch 151b between the threads is wide. With this structure, when the implant member is implanted in the maxilla and/or mandibula; the implant member 151 is threaded into the maxilla and/or mandibula in such a manner as to cut the maxilla and/or mandibula. Such an implantation produces only small resistance against the maxilla and/or mandibula, and therefore, the implant member 151 can be easily implanted in maxilla and/or mandibula without damaging its screw top.

EXAMPLE 16

Figure 29:
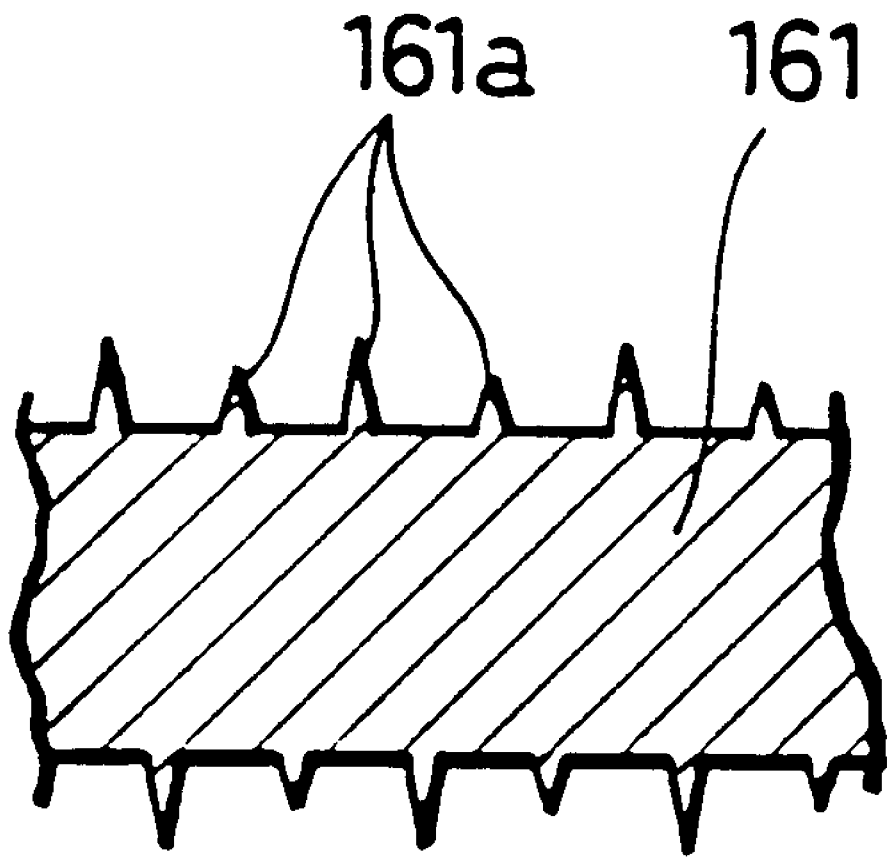
FIG. 29 is a diagram showing a supporting body for use in an orthodontic appliance according to Example 16 of the present invention.

FIG. 29 is a partially sectional view showing a part of an implant member 161 of a supporting body according to Example 16 of the present invention.

In Example 16, a supporting body has a structure identical to that of Example 15 except that the high and low screw threads 161a are alternately arranged on the surface of an implant member. With this arrangement, when the implant member 161 is threaded into the maxilla and/or mandibula, the low screw threads 161a are not brought into contact with the maxilla and/or mandibula. Therefore, no contact resistance is generated between the low screw threads 161a and the maxilla and/or mandibula. In this manner, the resistance generated between the entire implant member 161 and the maxilla and/or mandibula is decreased, so that the implant member 161 can be easily implanted into maxilla and/or mandibula without damaging its screw end.

EXAMPLE 17

Figure 30A:
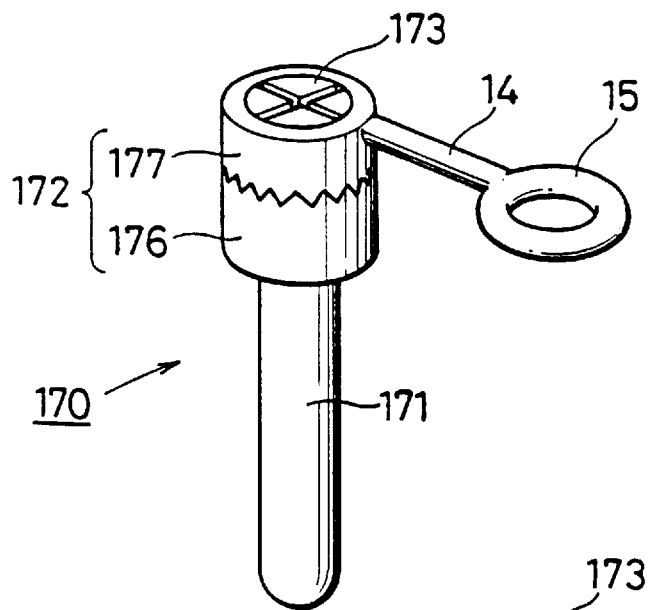
FIG. 30 is a perspective view showing a supporting body for use in an orthodontic appliance according to Example 17 of the present invention.
Figure 30B:
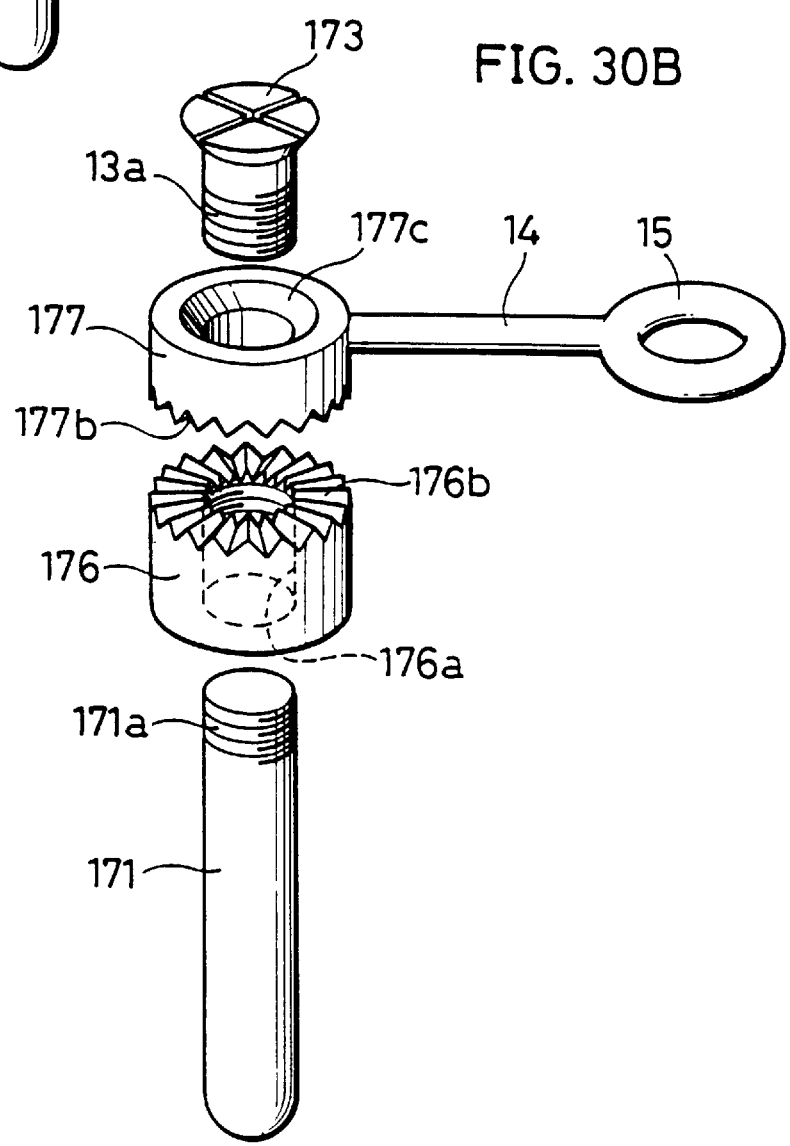

FIG. 30A is a perspective view showing a supporting body according to Example 17 of the present invention. FIG. 30B is a perspective view showing the members forming the supporting body. FIG. 31 is a longitudinal sectional view of the supporting body.

In Example 17, a supporting body 170 includes an implant member 171, an abutment (an exposed member) 172 to be exposed inside of mouth when in use, and a screw 173 for fixing the implant member 171 and the abutment 172 to each other. The abutment 172 consists of the upper member 177 and the lower member 176 which are engageable to each other. The upper member 177 has an arm 14 formed with a hook 15 on its end.

A bottom surface 177b of the upper member 177 and the top surface of the lower member 176 are formed with a plurality of projections and recesses arranged alternately in a radial direction. This structure enables a teeth engagement between the upper member 177 and the lower member 176, so that the orientations of the upper member 177 having the arm 14 is adjustable along a horizontal direction at a fine pitch per projection and recess. Accordingly, the arm 14 can be oriented more precisely in a desirable direction.

The upper member 177 has a hole 177c penetrating its center position, and the lower member 176 has a female screw portion 176a penetrating its center position. The implant member 171 is formed with screw threads on its top end. The upper member 177 and the lower member 176 are firmly fixed to each other by the screw 173 through the hole 177c and the female screw portion 176a. The implant member 171 is firmly fixed to the abutment 172 by threading its leading end into the female portion 176a formed in the lower member 176.

Although the present invention has been described by way of Examples 1 to 17 referring to drawings, it is understood that the present invention is not limited thereto and modification and variation of the present invention is possible without departing from the spirit or scope of the invention.

For example, the diameter and length of the implant member, the length of the arm, the angle formed between the axial centers of the implant member and the axial centers of the arm and the like are not limited to those described in Examples 1 to 17, but are variable to be optimally adapted to a patient. When a supporting body has an arm which is not made of spring plate as is the case of Examples 1 to 9, 12, and 15, it is recommended that the arm has a length in a range between 1.5 to 5 mm.

Furthermore, in Examples 1 and 2, the implant member has a round-shaped cross-section on a plane perpendicular to the axial center thereof, as shown in FIGS. 2B and 4B; however, the cross-section is not limited to a round shape, but may be of an elliptical shape, a triangular shape, and the like. When an implant member has a triangular cross-section and is formed with screw threads on its outer surface, the distance between screw threads and the axial center of the implant member is smaller at a side of the triangle than at an apex thereof. When thus-formed implant member is implanted into maxilla and/or mandibula, the screw threads present at each side of the implant member are not brought into contact with the maxilla and/or mandibula, and no contact resistance is generated between the implant member and the maxilla and/or mandibula. Accordingly, as is the case of Example 16, the resistance between the entire implant member and the maxilla and/or mandibula is decreased.

In Example 15, the supporting body of the first invention, which is implanted to maxilla and/or mandibula without piercing it, has been described. However, Example 15 may be applied to the supporting body of the second invention, which pierces the maxilla and/or mandibula. That is, the supporting body of the second invention may have an implant member formed with screw threads on its outer surface, in order that the implant member is firmly fixed to the maxilla and/or mandibula.

The exposed height of the exposed member (an abutment) inside of mouth when in use is not limited to a specific value. Preferably, the exposed height is as low as possible. Whereas some exposed height is necessary for an orthodontic treatment, a small exposed height gives only a small sense of discomfort to a bucca and tongue and gives only a small force to an implantation site where a supporting body is implanted. When a supporting body has an arm of which axial center forms an obtuse angle or 180 degree with the axial center of an implant member, the exposed height of the exposed member (or the abutment) becomes large. In this case, it is preferable that the portion of the exposed member (or the abutment) other than the portion having the arm has a height in a range between 1.5 and 3 mm.

In Examples 1 to 15 and 17, a hook has a ring shape or a C-shape; however, it is not limited thereto. A hook may have any shape as far as it can be connected to a bracket, a lingual button, a resin chain, a metallic coil spring, and the like. It is preferable to select a hook having such a shape that gives less sense of discomfort to bucca and tongue. In addition, the arm may be in an oval shape formed with a hook on its end to which a resin chain is engaged.

In Examples 1 and 2, the implant member 11 has a hexagonal shape projection and the abutment 12 has a hexagonal shape recess which are engageable to each other; however, it is not limited thereto, and these recess and projection may be formed in a polygonal shape so as to be oriented to a desired horizontal direction. For example, in the case of an octagonal shape, the direction of the orientation of the arm can be horizontally changed by 45 degree.

In Examples 1 to 16, an abutment (i.e., an exposed member) and an implant member are independently formed; however, they may be formed in one piece unit. When a supporting body includes an abutment and an implant member which are independently formed, it is possible to exchange an abutment into new one having an arm with a different length and/or a different upward direction from the old one. Accordingly, an abutment which is the most preferable for the patient can be selected and can be mounted to an implant member. In addition, this structure enables a position of a hook to be changed to a desired position even after implanting an implant member into maxilla and/or mandibula.

In Examples 1 to 16, an implant member is in one piece unit; however, it is not limited thereto. For example, an implant member may consist of two independent members, that is, a connecting part to be connected to an abutment and a implanted part to be implanted in the maxilla and/or mandibula, and these two members are combined into one piece unit when in use.

In Example 12, a supporting body 120 includes the abutments 122a and 122b each of which has an arm 124a and 124b respectively. In Example 13, a supporting body 130 includes the abutments 132a and 132b neither of which has an arm. However, it is not limited thereto, and a supporting body may have abutments only one of which has an arm.

In the pierce supporting body of Example 12, the hook is provided to the end of the respective arms. However, the hook may be provided at any portion of the arm. In addition, one abutment may have two or more arms.

Processes of implanting a supporting body into maxilla and/or mandibula

Figure 9:
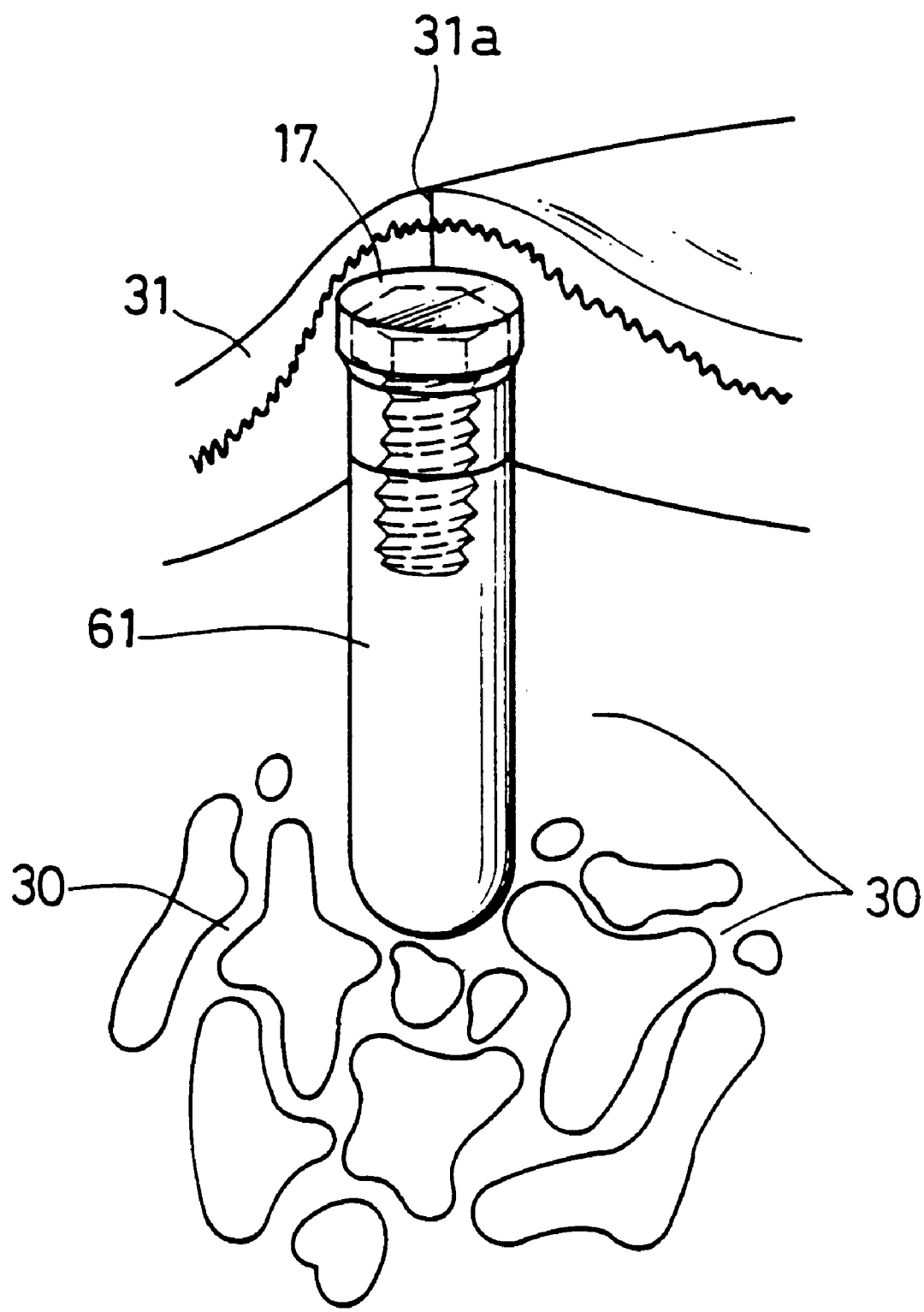
FIG. 9 is a partially sectional view for illustrating steps of implanting a supporting body of the present invention in a maxilla and/or mandibula.
Figure 10:
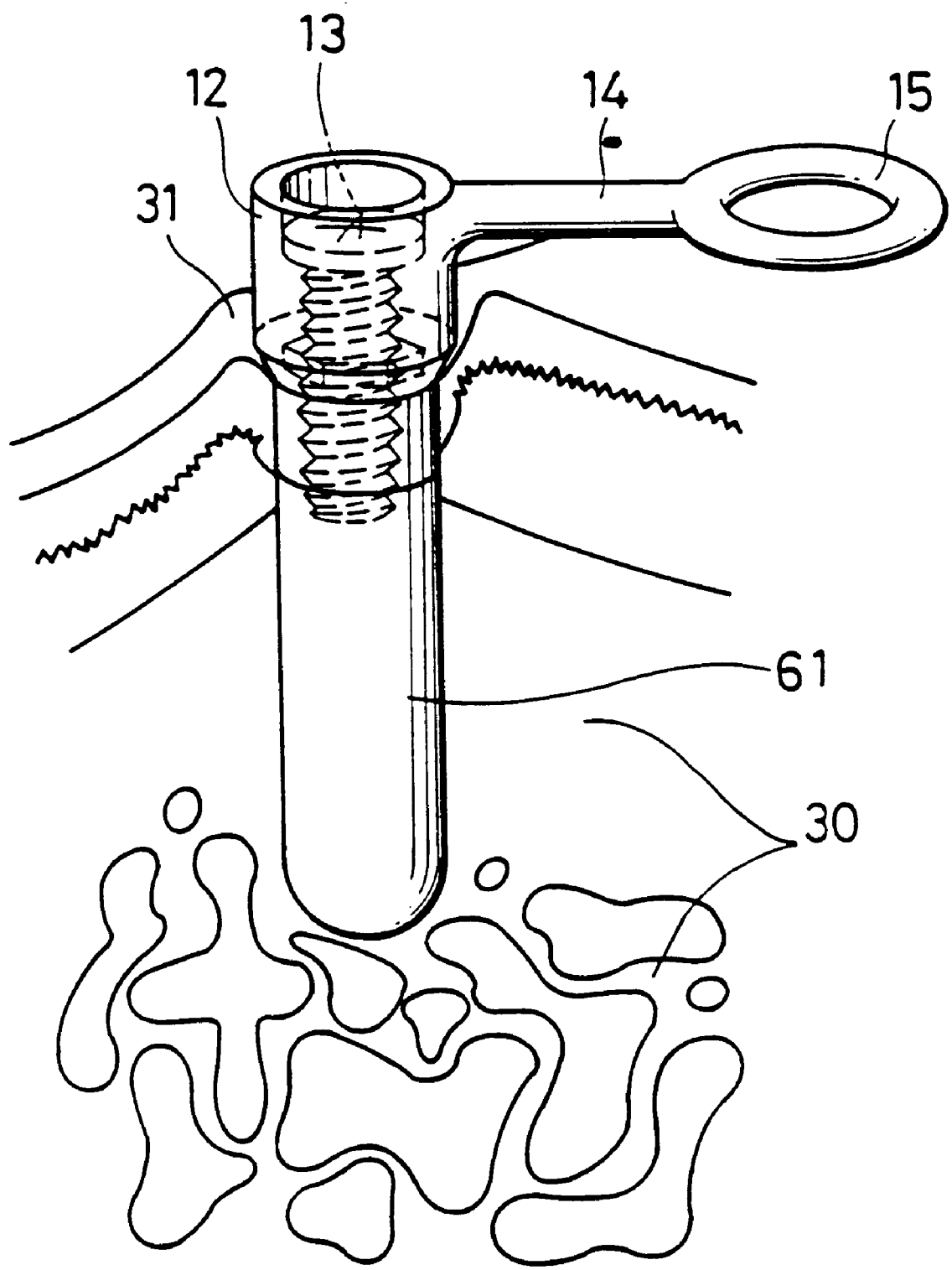
FIG. 10 is a partially sectional view for illustrating steps of implanting a supporting body of the present invention in a maxilla and/or mandibula.

Hereinafter, processes of implanting a supporting body in the maxilla and/or mandibula will be described referring to FIGS. 9 and 10. The processes will be described using a supporting body of Example 3 as an example.

Prior to implanting a supporting body 10 in the maxilla and/or mandibula, a recess (into which a projection of an abutment 12 is engaged) of an implant member 61 is covered with a temporary cap 17. Then, gingival mucosa is cut open and maxilla and/or mandibula is drilled to form a hole using an appliance such as a drill. The implant member 61 of the supporting body 10 is fitted into the hole. After that, an opening 31a of the gingival mucosa is stitched. The implant member 61 is left in this state until the stitched portion is cured and the implant member 61 is firmly fixed to the maxilla and/or mandibula 30 (see FIG. 9), in order to prevent the implantation site from being contaminated by bacteria.

When the gingival mucosa 31 has grown to cover the implant member 61 and the implant member 61 is firmly fixed to the maxilla and/or mandibula 30, the gingiva mucosa 31 covering the implant member 61 is removed. Then, an abutment 12 is mounted to the implant member 61 and is fixed thereto by a screw 13 (see FIG. 10).

In the above description, the maxilla and/or mandibula 30 is drilled to form a hole for implanting an implant member 61. Or alternatively, an implant member 61 may be implanted in the maxilla and/or mandibula without previously forming a hole upon cutting the gingival mucosa 31, because the implant member has a small diameter.

When an orthodontic treatment will take only a short period of time and there is no fear that the stitched implantation site is contaminated by bacterial, the abutment 12 may be mounted to the implant member 61 immediately after implanting the implant member 61 in the maxilla and/or mandibula 30 without waiting until the stitched implantation site is cured.

In addition, when there is no fear that the stitched implantation site will not be contaminated by bacterial because, for example, an antibiotic substance is applied thereto or a supporting body having extremely small diameter is to be used, a supporting body including an implant member and an exposed member formed in one piece unit is can be used. In this case, the supporting body is implanted while its exposed member is exposed inside of mouth without stitching the wound. Then, the supporting body is left in this state until its implant member is firmly fixed to the maxilla and/or mandibula.

DESCRIPTION OF AN ORTHODONTIC TREATMENT

Hereinafter, an orthodontic treatment using the supporting body of the present invention will be specifically described.

Treatment Example 1

Figure 11:
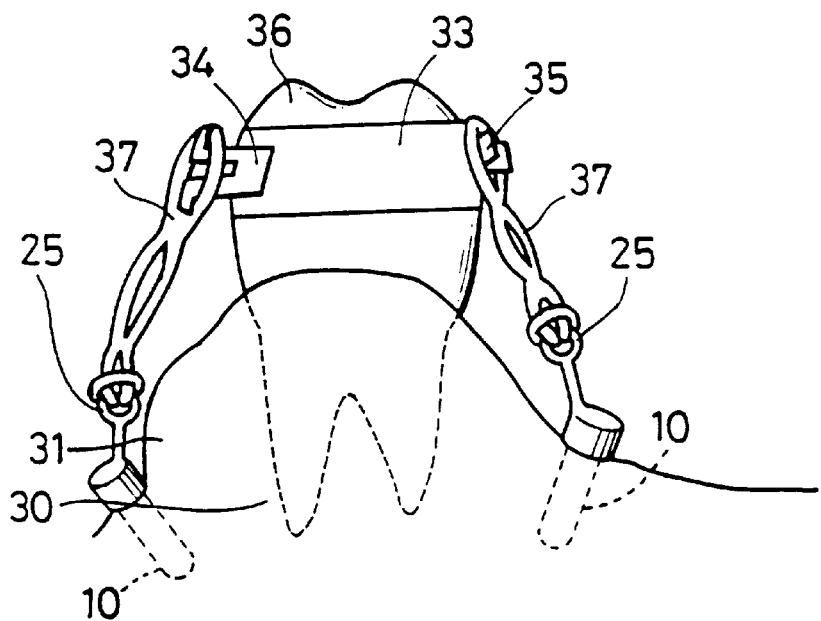
FIG. 11 is a diagram for illustrating an orthodontic treatment 1 using the supporting body of the present invention.

FIG. 11 is a diagram for illustrating a method for pulling a molar tooth toward alveolus. In Treatment Example 1, used is a supporting body with an implant member having only one arm on its one end, as those of Examples 1 to 7.

A band 33 is fitted to a molar tooth 36, and the band 33 is attachedly provided with a bracket 34 and a lingual button 35. At the same time, supporting bodies 10 are implanted to maxilla and/or mandibula 30 on the left and right sides of the molar tooth 36. Each supporting body 10 is provided with a hook 25 via an 15 arm. The hooks 25 are connected to the bracket 34 and the lingual button 35, respectively by a resin chain 37. In this state, an elastic force is applied to the molar tooth 36 through the resin chain 37, thereby pulling the molar tooth 36 toward the alveolus to a desired position.

The implantation site of the supporting bodies 10 may be limited to a specific region depending on the presence or absence of nerves, and therefore, may be deviated from the position which is the most preferable for conducting an orthodontic treatment.

This problem can be solved by selecting a supporting body having an arm with a desired length and then placing the supporting body while orienting the arm to the desired direction. In this manner, a hook can be located at the most preferable position for applying a force to the tooth to be treated.

Treatment Example 2

Figure 12:
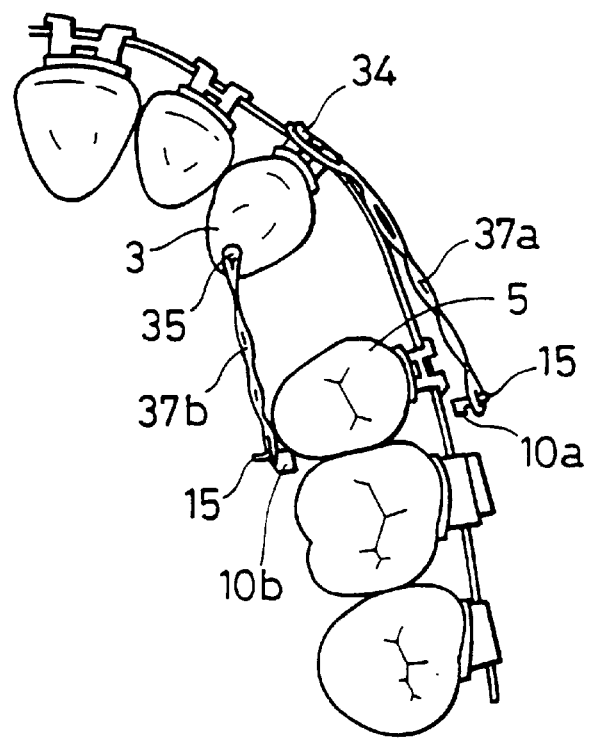
FIG. 12 is a diagram for illustrating an orthodontic treatment 2 using the supporting body of the present invention.

FIG. 12 is a diagram for illustrating a method for treating a canine tooth. In FIG. 12, the arrangement of the teeth on upper left jaw is shown. In Treatment Example 2, the canine tooth is centrifugally moved. As in the case of Treatment Example 1, used is a supporting body having only one arm on its one end, as those of Examples 1 to 7.

In Treatment Example 2, a tooth 3 (a canine tooth) is pulled toward a tooth 5 (the fifth premolar tooth). In the vicinity of the tooth 5 on the buccal side and on the lingual side, supporting bodies 10a and 10b are respectively implanted. The tooth 3 has attached thereto a bracket 34 and a lingual button 35. The supporting body 10a is connected to the bracket 34 by a resin chain 37a, and the supporting body 10b is connected to the lingual button 35 by a resin chain 37b. In this state, the tooth 3 is pulled toward the tooth 5 while the pulling force is uniformly applied to the tooth 3. In this manner, the tooth 3 is moved to a desired position without being irregularly twisted.

The implantation site of the supporting bodies 10a and 10b may be limited to a specific region depending on the presence or absence of nerves, and therefore, may be deviated from a position which is the most preferable for orthodontic treatment. This problem can be solved by selecting a supporting body having an arm with a desired length and then placing the supporting body while orienting the arm to the desired direction. In this manner, the hook can be located at the most preferable position for applying a force to the tooth to be treated. In addition, the hook also can be located at such a position as to prevent the contact between the resin chain and the alveolus.

Treatment Example 3

FIG. 13 is a front diagram for illustrating a method for treating a front tooth 1. In the treatment, the front tooth 1 is pulled toward the alveolus. In Treatment Example 3, a supporting body 10 of Example 6 is used as an example.

When the implantation site of the supporting body 10 is limited to a position between a front tooth 1 and a front tooth 2 due to the presence of nerves (i.e., at a position same as that in the conventional case), it is possible to locate a hook 65 at any position along the direction shown by an arrow K via an arm 64. The front tooth 1 is provided with a bracket 34. The hook 65 and the bracket 34 are connected to each other to apply a pulling force to the front tooth 1 along the direction K. In this manner, the front tooth 1 is moved to a desired position.

When an orthodontic treatment is conducted using the supporting body of the present invention, a force can be applied to the tooth to be treated from the most preferable position along the most preferable direction. Therefore, there is no need to utilize a complicated processes such as connecting the tooth to be treated to the other tooth, and the treatment takes only a short period of time.

Treatment Example 4

Figure 18:
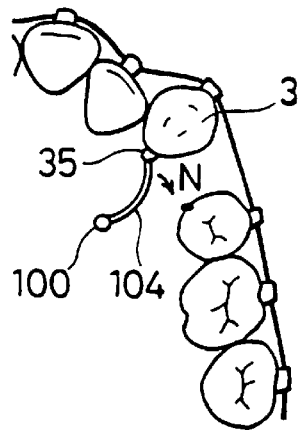
FIG. 18 is a diagram for illustrating an orthodontic treatment 4 using the supporting body of the present invention.

FIG. 18 is a diagram for illustrating a method for treating a canine tooth, as is the case of Treatment Example 2. In FIG. 18, the arrangement of the teeth on upper right jaw is shown. In Treatment Example 4, the canine tooth is centrifugally moved, and used is a supporting body having an arm made of a spring plate of Example 10.

A supporting body 100 is implanted in an upper palatal bone, and a tooth 3 is provided with a lingual button 35 on its lingual side. As shown in FIGS. 17 and 18 (especially by a dashed line in FIG. 17), while curving an arm 104 of the supporting body 100, a hook 105 on the end of the arm 104 is engaged to a lingual button 35. In this state, a restoring force generated by the arm made of spring plate is applied to the tooth 3 thereby centrifugally moving the tooth 3 in a direction shown by an arrow N.

Treatment Example 5

Figure 20:
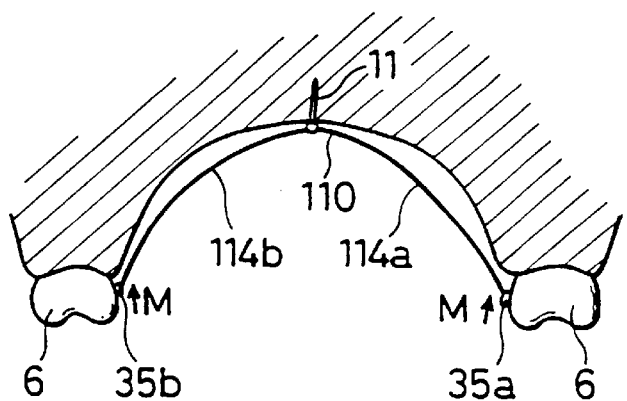
FIG. 20 is a diagram for illustrating an orthodontic treatment 5 using the supporting body of the present invention.

FIG. 20 is a diagram for illustrating a method for simultaneously treating two teeth. In FIG. 20, a cross section of an upper jaw is shown. In Treatment Example 5, two teeth are pulled toward alveolus using a supporting body 110 having two arms made of plate spring.

Each of arms 114a and 114b are formed with hooks 115a and 115b on their respective ends, and two teeth 6 are attachedly provided with lingual buttons 35a and 35b respectively on their lingual sides. The supporting body 110 is implanted in an upper palatal bone. As shown in FIGS. 19A and 20 (especially shown by a dashed line in FIG. 19A), while curving the arms 114a and 114b, the hooks 115a and 115b are engaged to the lingual buttons 35a and 35b respectively. A restoring force generated by the arms 114a and 114b is applied to the two teeth 6, thereby pulling the two teeth 6 along a direction shown by an arrow M.

Treatment Example 6

Figure 22A:
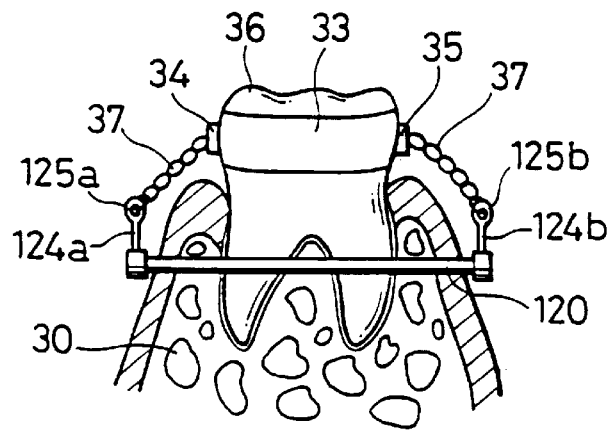
FIG. 22 is a diagram for illustrating an orthodontic treatment 6 using the supporting body of the present invention.
Figure 22B:
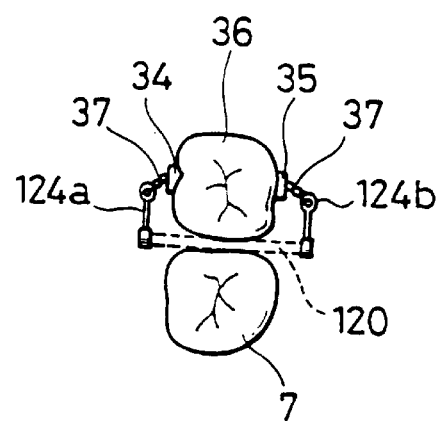

FIG. 22 is a diagram for illustrating a method for treating a molar tooth as is the case of Treatment Example 1. FIG. 22A is a side view showing the gingiva and maxilla and/or mandibula. FIG. 22B is a top view of FIG. 22A. In Treatment Example 6, used is a pierce supporting body 120 of Example 12.

As is the case of Treatment Example 1, a band 33 is fitted to a molar tooth 36. The band 33 is attachedly provided with a bracket 34 and a lingual button 35. An implant member 121 of the supporting body 120 pierces the maxilla and/or mandibula 30 between a tooth 36 and a tooth 7 adjacent to the tooth 36 in such a manner that the nerve, tooth 36, and a dental root are not damaged.

The hooks 125a and 125b are connected to the bracket 34 and the lingual button 35 respectively via resin chains 37. The resin chain 37 pulls the tooth toward the alveolus.

In this case, by selecting the most preferable length and upward angle of the arm 124a and 124b, the hooks 125a and 125b on each end of the arms 124a and 124b are located at the most preferable position to be used as an anchorage. In addition, the tooth 36 can be uniformly pulled by the resin chains 37 via the bracket 34 and the lingual button 35, thereby pulling the tooth 36 toward the alveolus without being irregularly twisted.

As a bone is repeatedly destroyed and built, there is a fear that the implant of the supporting body 10 is gradually inclined when it receives a force during the treatment of Treatment Example 1. However, in Treatment Example 6, the pierce supporting body 120 of Example 12 is used, so that the implant member thereof receives a uniform force. Therefore, there is no fear that the implant member 121 is inclined.

Treatment Example 7

Figure 24:
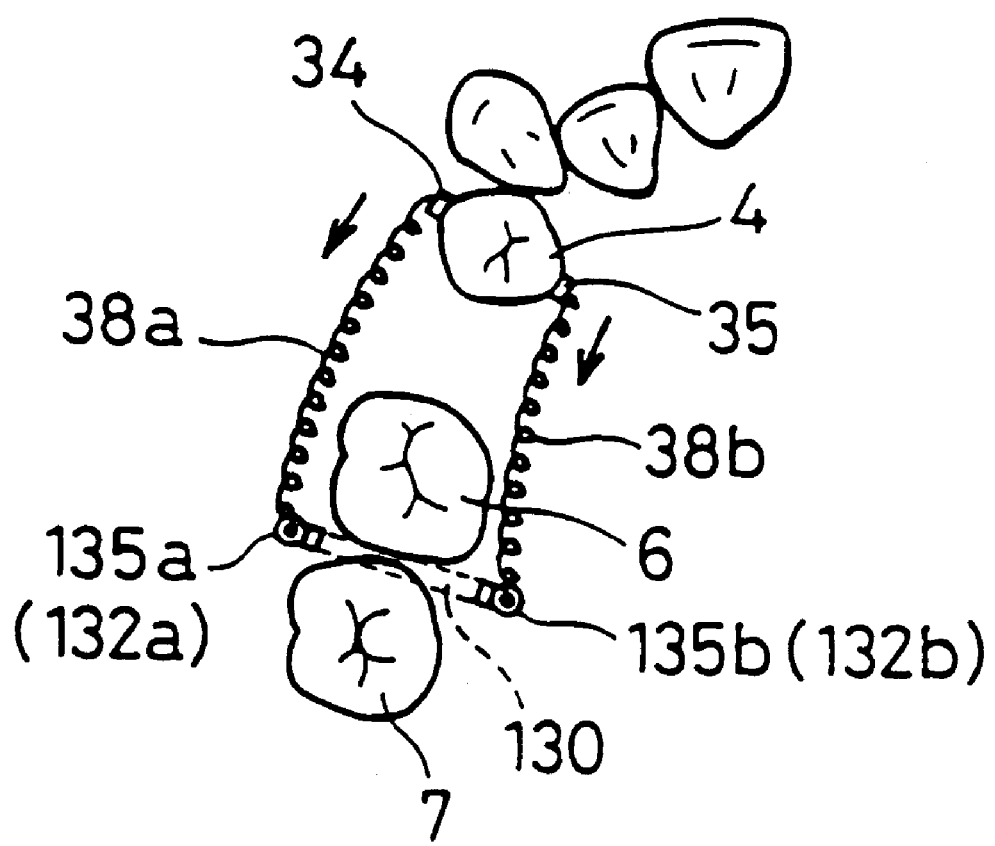
FIG. 24 is a diagram for illustrating an orthodontic treatment 7 using the supporting body of the Example 13 shown in FIG. 23.

FIG. 24 is a diagram for illustrating a method for treating the fourth premolar tooth. In FIG. 24, the arrangement of the teeth on upper right jaw is shown. In Treatment Example 7, the fourth premolar tooth is centrifugally moved using a pierce supporting body 130 of Example 13.

The supporting body 130 pierces the maxilla and/or mandibula between teeth 6 and 7. A tooth 4 (forth premolar tooth) is attachedly provided with a bracket 34 on its buccal side, and a lingual button 35 on its lingual side.

The supporting body 130 has an abutment 132a exposed on the buccal side and an abutment 142b exposed on the lingual side, each of which is formed with a hook 135a and 135b respectively. The hook 135a is connected to the bracket 34 by a coil spring 38a, and the hook 135b is connected to the lingual button 35 by a coil spring 38b.

The coil springs 38a and 38b pull the fourth premolar tooth 4 via the bracket 34 and the lingual button 35 in a direction shown by an arrow in FIG. 24 using the hooks 135a and 135b as an anchorage. In this manner, the fourth premolar tooth 4 is moved to a desired position without being irregularly twisted.

In Treatment Example 7, used is the supporting body 130 having no arm of Example 13; however, the supporting body 120 having arms of Example 12 can be also used. When the supporting body 120 having arms is used, the orientation of the arms are properly changed in order that the hooks are located at a desired position for conducting a treatment and that a coil spring for connecting the hook and the bracket to each other is not brought into contact with the alveolus.

Treatment Example 8

Figure 26:
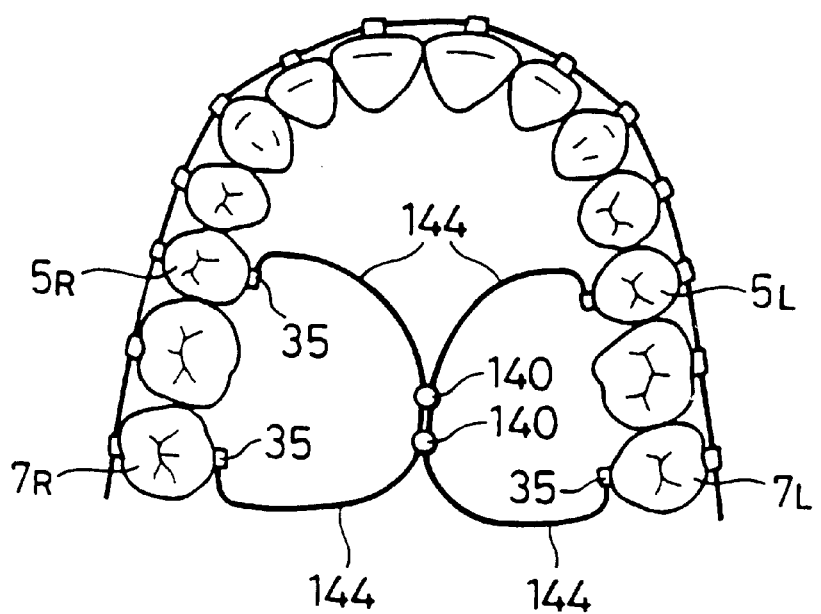
FIG. 26 is a diagram for illustrating an orthodontic treatment 8 using the supporting body of the Example 14 shown in FIG. 25.

FIG. 26 is a diagram for illustrating a method for simultaneously treating four teeth. In FIG. 20, a cross section of an upper jaw is shown. In Treatment Example 8, two supporting bodies 110 have four arms in common are used.

In Treatment Example 8, two supporting bodies 140 are implanted in an upper palatal bone, and these two supporting bodies 140 have four arms 144 in common. Each arm 144 is made of plate spring, and is formed with a hook on its end. Each of teeth $5_R$, $7_R$, $5_L$, and $7_L$ is attachedly provided with a lingual button 35. Each hook is engaged to each lingual button 35. In this state, the restoring force generated by the arms 144 is applied to the teeth $5_R$, $7_R$, $5_L$, and $7_L$ thereby moving them to a desired position.

In Treatment Example 8, two supporting bodies are implanted in an upper palatal bone (that is, there are two implantation sites.). A plurality of supporting bodies together can endure a stronger force during the treatment. However, only one supporting body is used for simultaneously treating four teeth.

Treatment Example 9

Figure 27:
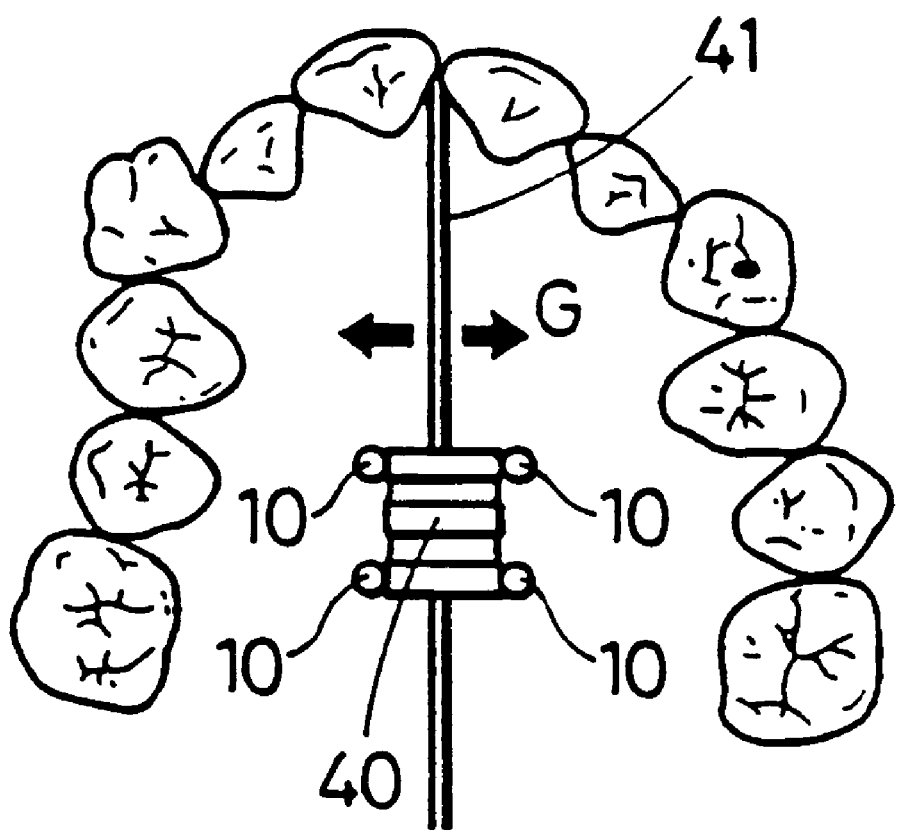
FIG. 27 is a diagram for illustrating an orthodontic treatment 9 using the supporting body of the present invention.

FIG. 27 is a diagram for opening the median palatine suture toward both buccal sides. In FIG. 27, an upper jaw is shown.

The supporting body of the present invention can be used in a treatment for opening the median palatine suture toward both buccal sides. A plurality of supporting bodies 10 are implanted in an upper palatal bone, each of which is connected to a rapid expansion appliance 40. The rapid expansion appliance 40 generates a pushing force toward both buccal sides, and the force is conveyed to the upper palatal bone via the supporting bodies 10, thereby opening the upper platal bone toward the buccal sides.

Conventionally, the expansion appliance is set to the teeth, and the force is applied to the teeth to open the median palatine suture toward both buccal sides. Contrary to this, according to the present invention, the supporting bodies are implanted in an upper palatal bone, and the force is directly applied to the upper palatal bone. In this manner, the median palatine suture 41 can be expanded without giving no stress to teeth.

Although the present invention has been described by way of Examples 1 to 16 referring to drawings, it is understood that the present invention is not limited thereto and modification and variation of the present invention is possible without departing from the spirit or scope of the invention.

In Treatment Examples 1 to 3 and 6, a pulling force toward the supporting body is generated by a resin chain. In Treatment Example 7, a pulling force toward the supporting body is generated by a resin chain. However, it is not limited thereto, and a pushing force against the supporting coil may be generated by a coil spring. In any of these methods, the supporting body of the present invention can be used.

When the treatment is completed, the supporting body is removed from the implantation site. However, as the supporting body of the present invention has small diameter, there is no problem for human body even if the supporting body is not removed and is left implanted.

As described above, the supporting body of the present invention can be implanted to maxilla and/or mandibula while avoiding nerves. When the supporting body has an arm of which orientation is changeable, the hook provided to the arm can be located at a desired position. In addition, the implant member has small diameter, so that the wide selection of the implantation site can be obtained.

By adjusting the orientation of the arm so as to locate the hook to the most preferable position for applying a force to the tooth to be treated, the tooth is moved along a straight line toward the supporting body. Accordingly, no complicated processes are required contrary to the conventional cases. In this manner, an orthodontic treatment requires only short period of time and only small burden is given to a patient. In addition, the supporting body of the present invention is also applicable in a treatment in which the median palatine suture is expanded without giving no harmful influence to teeth.

Although the present invention has been fully described by way of examples with reference to the accompanied drawings, it is to be understood that various changes and modifications will be apparent to those skilled in the art. Therefore, unless otherwise such changes and modifications depart from the scope of the invention, they should be construed as being included therein.

What is claimed is:

1. A supporting body for use in an orthodontic appliance comprising:
    an implant member having a maximum dimension of 2 mm or less in a cross section thereof for being implanted in a jaw bone at an implant site; and
    an exposed member forming one end of the supporting body to be exposed to an inside portion of a mouth when in use the exposed member comprising an arm connected thereto and a hook connected to said arm such that said hook is spaced a predetermined distance from said implant site of said implant member so as to permit application of a force to said hook whereby application of force to a tooth to be treated can be conducted from a preferable position distanced from the implant site.

2. The supporting body according to claim 1, wherein the implant member and the exposed member are independently formed from each other and the exposed member is mountable to the implant member to form a one piece unit when in use.

3. The supporting body according to claim 2, further comprising a screw member for screw connecting the implant member and the exposed member.

4. The supporting body according to claim 2, wherein the exposed member is formed with a polygonal shape recess and one end of the implant member is formed with a corresponding polygonal shape projection fitting to the polygonal shape recess whereby the arm is selectably oriented in a plane perpendicular to the axial direction of the implant member.

5. The supporting body according to claim 2, wherein the exposed member is provided with a teeth engageable portion and the implant member is provided with a teeth engaging portion that is engageable with the teeth engageable portion so that the arm is selectably oriented in a plane perpendicular to the axial direction of the implant member.

6. The supporting body according to claim 2, wherein the exposed member has a tapered surface with respect to the longitudinal axis of the supporting body and the implant member has a corresponding tapered surface whereby the exposed member is fitted to the implant member.

7. The supporting body according to claim 1, wherein an angle formed between the axial centers of the arm and the implant member is set in a range of 90 degrees and 180 degrees.

8. The supporting body according to claim 7 wherein the exposed member having a polygonal shape projection is fitted to the implant member having a polygonal shape recess whereby the arm is selectably oriented in a plane perpendicular to the axial direction of the implant member.

9. The supporting body according to claim 7, wherein the exposed member has a tapered surface with respect to the longitudinal axis of the supporting body and the implant member has a corresponding tapered surface whereby the exposed member is fitted to the implant member.

10. The supporting body according to claim 1, which comprises a mechanism permitting adjustment of a length dimension of the arm.

11. A supporting body according to claim 10, wherein the arm is slidable in a lengthwise direction thereof such that the length of the arm from the implant member is adjustable.

12. The supporting body according to claim 1, wherein the exposed member has a plurality of arms.

13. The supporting member according to claim 1, wherein the arm is made of a plate spring.

14. A supporting body according to claim 1, wherein the arm comprises a plurality of rings.

15. The supporting body for use in an orthodontic appliance, the supporting body comprising:
   an implant member to pierce a jaw bone, said implant member having opposite ends; and
   an exposed member provided on each of said opposite ends of the implant member to be exposed to inside of mouth when in use, each of said exposed members having a hook.

16. The supporting body according to claim 15, wherein the implant member has the maximum dimension of 2 mm or less in its cross sectional view.

17. The supporting body according to claim 15, wherein the implant member and the exposed member are independently formed from each other, and the exposed member is mountable to the implant body to form a one piece unit when in use.

18. The supporting body according to claim 17, wherein the exposed member having a polygonal shape projection is fitted to the implant member having a polygonal shape recess wherein the exposed member is selectably oriented to a plane perpendicular to the axial direction of the implant member.

19. The supporting body according to claim 15, wherein the hook is connected to the exposed member via an arm.

20. The supporting body according to claim 19, wherein an angle formed between the axial centers of the arm and the implant member is set in a range between 90 degrees and 180 degrees.

21. The supporting body according to claim 15, wherein the exposed member has a plurality of arms.

22. The supporting body according to claim 15, wherein the exposed member has an arm made of a plate spring.

23. An orthodontic method using a supporting body including an implant member having a maximum dimension of 2 mm or less across a cross section thereof and an exposed member forming one end of the supporting body, the orthodontic method comprising the steps of:
   attaching to the implant member an arm having a hook such that the hook is spaced a predetermined distance from the implant member, the orthodontic method comprising the steps of:
      a) implanting the implant member in a jaw bone;
      b) attaching a fixing member to a tooth to be treated;
      c) connecting the fixing member and the hook by an elastic member; and
      d) applying an elastic force to the tooth, said force being generated by the elastic member whereby application of force to the tooth to be treated can be conducted from a preferable position distanced from the implant site.

24. An orthodontic method using a supporting body including an implant member having a maximum dimension of 2 mm or less across a cross section thereof and an exposed member forming one end of the supporting body, the exposed member including an extended arm made of a plate spring wherein the arm is formed with a hook, the orthodontic method comprising the steps of:
   (a) implanting the implant member in a jaw bone;
   (b) attaching a fixing member to a tooth to be treated;
   (c) engaging the hook with the fixing member; and
   (d) applying a force to the tooth, said force being generated by the arm.

25. An orthodontic method using the supporting body comprising an implant member to be pierce a jaw bone and an exposed member having a hook provided on opposite ends of the implant body to be exposed to inside of mouth, the orthodontic method comprising the steps of:
   a) implanting the implant member of an orthodontic appliance in such a manner as to penetrate through a jaw bone;
   b) attaching a fixing member to a tooth to be treated;
   c) connecting the fixing member and the hook by an elastic member; and
   d) applying a force to the tooth, said force being generated by the elastic member.

26. A supporting body for use in an orthodontic appliance comprising:
   an implant member having a maximum dimension of 2 mm or less across a cross section thereof for being implanted in a jaw bone at an implant site; and
   an exposed member forming one end of the supporting body to be exposed to an inside portion of a mouth of a user of the appliance when in use, the exposed member comprising an arm extending in a direction so as to form an angle of greater than 0 degrees and less then 180 degrees with respect to a longitudinal axis of the implant member, and a hook connected to the arm, said hook being located at a position apart from the longitudinal axis of the implant member and spaced from said implant site by a predetermined distance whereby application of force to a tooth to be treated can be conducted from a preferable position distanced from the implant site.

27. An orthodontic method using a supporting body including an implant member having a maximum dimension of 2 mm or less across a cross section thereof and an exposed member forming one end of the supporting body, the exposed member including an arm extending in a direction so as to form an angle of greater than 0 degrees and less then 180 degrees with respect to an longitudinal axis of the implant member, and the arm being formed with a hook at the position apart from the longitudinal axis of the implant member, the orthodontic method comprising the steps of:

a) implanting the implant member in a jaw bone:

b) attaching a fixing member to a tooth to be treated;

c) connecting the fixing member and the hook by an elastic member; and d) applying an elastic force to the tooth, said force being generated by the elastic member.

* * * * *